United States Patent
Zhao et al.

(10) Patent No.: US 10,689,463 B2
(45) Date of Patent: Jun. 23, 2020

(54) FUC3S4S SUBSTITUTED OLIGOGLYCOSAMINOGLYCAN AND PREPARATION METHOD THEREOF

(71) Applicant: JIUZHITANG CO., LTD., Changsha, Hunan (CN)

(72) Inventors: Jinhua Zhao, Kunming (CN); Jinxing He, Yuxi (CN); Mingyi Wu, Kunming (CN); Zhiwen Liu, Yuxi (CN); Na Gao, Kunming (CN); Longyan Zhao, Kunming (CN); Zi Li, Kunming (CN); Feng Lu, Kunming (CN); Li Xu, Kunming (CN); Chuang Xiao, Kunming (CN); Lian Yang, Kunming (CN); Jun Chen, Kunming (CN); Lutan Zhou, Kunming (CN); Wenlie Peng, Kunming (CN); Jikai Liu, Kunming (CN)

(73) Assignee: JIUZHITANG CO., LTD., Changsha, Hunan (CN)

( * ) Notice: Subject to any disclaimer, the term of this patent is extended or adjusted under 35 U.S.C. 154(b) by 311 days.

(21) Appl. No.: 15/110,664

(22) PCT Filed: Dec. 19, 2014

(86) PCT No.: PCT/CN2014/094417
§ 371 (c)(1),
(2) Date: Jul. 8, 2016

(87) PCT Pub. No.: WO2015/103921
PCT Pub. Date: Jul. 16, 2015

(65) Prior Publication Data
US 2016/0347868 A1    Dec. 1, 2016

(30) Foreign Application Priority Data
Jan. 8, 2014    (CN) .......................... 2014 1 0007855

(51) Int. Cl.
*C08B 37/00*    (2006.01)

(52) U.S. Cl.
CPC ...... *C08B 37/0063* (2013.01); *C08B 37/0003* (2013.01)

(58) Field of Classification Search
None
See application file for complete search history.

(56) References Cited

U.S. PATENT DOCUMENTS

2010/0316640 A1*  12/2010  Sundaram ............ A61K 31/404
                                                                424/133.1
2015/0051165 A1*   2/2015  Wang .................. C08B 37/0063
                                                                514/42

FOREIGN PATENT DOCUMENTS

CN          102558389 A  *  7/2012  ........... A61K 31/737

* cited by examiner

*Primary Examiner* — Dale R Miller
(74) *Attorney, Agent, or Firm* — Maschoff Brennan; Jonathan M. Benns

(57) ABSTRACT

Disclosed are a Fuc3S4S substituted oligoglycosaminoglycan with a weight-average molecular weight (Mw) of about 4.5-9 kD, a pharmaceutical composition containing the Fuc3S4S substituted oligoglycosaminoglycan, a preparation method thereof and a use thereof in preparing medicines for preventing and/or treating thrombotic diseases.

18 Claims, 8 Drawing Sheets

FUC3S4S SUBSTITUTED OLIGOGLYCOSAMINOGLYCAN AND PREPARATION METHOD THEREOF

CROSS-REFERENCE TO RELATED APPLICATIONS

Figure 1:
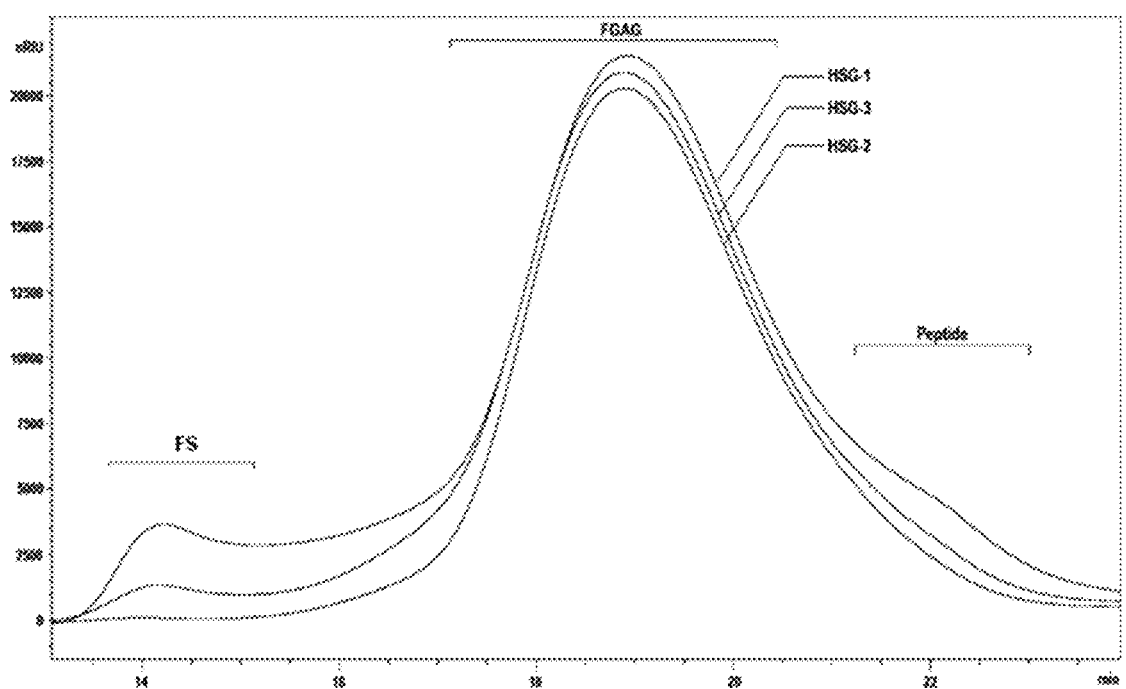

This application is the national phase of International Application No. PCT/CN2014/094417, filed Dec. 19, 2014, which claims the benefit of Chinese Patent Application No. 201410007855.7, filed with the Chinese State Intellectual Property Office on Jan. 8, 2014, the entire disclosures of the applications are incorporated herein by reference.

FIELD OF THE INVENTION

The present invention belongs to the field of medical technology, and relates to a Fuc3S4S substituted oligoglycosaminoglycan with a weight-average molecular weight (Mw) of about 4.5-9 kD and a pharmaceutically acceptable salt thereof, a pharmaceutical composition containing the Fuc3S4S substituted oligoglycosaminoglycan and/or a pharmaceutically acceptable salt thereof, a preparation method for preparing the Fuc3S4S substituted oligoglycosaminoglycan and the pharmaceutical compositions thereof and a use thereof in preparing medicines for preventing and/or treating thrombotic diseases.

BACKGROUND OF THE INVENTION

Fucosylated glycosaminoglycans (FGAGs) are a class of glycosaminoglycan derivatives having sulfated fucose branches obtained from the body wall of an echinoderm. FGAGs from different species in echinoderm or prepared by different methods have similarities but differences on chemical composition.

The similarities of FGAGs from different species are mainly manifested in that their monosaccharide compositions comprise D-2-acetylamino-2-deoxygalactose (D-GalNAc), D-glucuronic acid (D-GlcUA) and L-fucose (L-Fuc) and sulfate esters thereof, wherein, D-GlcUA and D-GalNAc are sequentially linked by β-(1-3) and β-(1-4) glycosidic linkages to form a backbone of glycosaminoglycan, and L-Fuc is linked to the backbone as a branch (Ricardo P. et al., JBC, 1988, 263 (34): 18176; Kenichiro Y. et al., Tetrahedron Lett, 1992, 33(34): 4959).

The differences in structure of FGAGs from different species mainly include different degrees and positions of sulfation of L-Fucs and different degrees and positions of sulfation in the backbones. Until now all reported sulfate substitutions of L-Fuc branches in FGAG are rather complicated. For example, FGAG from *Stichopus japonicas* mainly contains three types of L-Fuc, i.e., 2,4-disulfated (Fuc2S4S), 4-disulfated (Fuc4S) and 3,4-disulfated (Fuc3S4S), and Fuc2S4S makes up approximately ~60% of the total L-Fuc, while D-GalNAc on the backbone is mainly 4,6-disulfated (GalNAc4S6S) (Kenichiro Y, et al. *Tetrahedron Lett*, 1992, 33: 4959). The L-Fuc type of FGAG from *Holothuria leucospilota* has not been determined yet, and D-GalNAc on its backbone contains 4-sulfated (GalNAc4S) (Huizeng Fan, et al., *Acta Pharmaceutica Sinica*, 1983, 18 (3): 203). The L-Fuc of FGAG from Brazilian *Ludwigothurea grisea* comprise Fuc4S (~49%), Fuc2S4S (~20%), –3S4S (~17%) and L-Fuc without sulfate substitution (Fuc0S), and the D-GalNAc types of the backbone include GalNAc6S (~53%), –4S6S (~12%) and –4S (31%) (Lubor B. et al. *J. Biol. Chem.* 2007, 282:14984). The L-Fuc of FGAG from *Thelenata ananas* include Fuc2S4S (~53%), –4S (~22%), –3S (~25%), and the D-GalNAc contained is mainly GalNAc4S6S (~95%) and –6S (~5%) (Wu M., et al. *Carbohydr. Polym.*, 2012, 87(1): 862). The L-Fuc in FGAG from *Isostichopus badionatus* is mainly Fuc-2S4S (~96%). The composition of L-Fuc of FGAG from *Holothuria vagabunda* is similar to the Brazilian sea cucumber. The FGAGs from *Stichopus tremulus* include Fuc3S4S (~53%), –2S4S (~22%) and –4S (~25%) (Chen S G, et al. *Carbohydr. Polym.*, 2011, 83 (2): 688).

FGAGs from various sea cucumbers have potent anticoagulant activity (Peiwen Zhang, *Chinese Journal of Pharmacology and Toxicology*, 1988, 2(2): 98; Paulo A S. et al., *J. Biol. Chem.* 1996, 271: 23973). However, these native FGAGs also have platelet aggregation-inducing activity (Jiazeng L. et al, *Thromb Haemos*, 1988, 54(3): 435; Chunwen Shan, *Pharmacology and Clinics of Chinese Materia Medica*, 1989, 5(3): 33) and surface activation activity of activation factor XII (Roberto J. et al. *Thromb Haemost.* 2010, 103:994). For the FGAG from *Stichopus japonicus*, the DHG obtained by depolymerization can weaken platelet aggregation-inducing activity (Hideki N. et al., *Blood*, 1995, 85 (6):1527).

The studies on pharmacological mechanism of anticoagulant activity of FGAG from sea cucumber show that, FGAG has mechanism characteristics different from those of heparin anddermatan sulfate. For example, FGAG, as a potent F.Xase inhibitor, may inhibit the activation on factor X by endogenous factor X enzyme. It has an ATIII- and HCII-dependent antithrombin activity. It has an inhibition activity on feedback activation of factor XIII by thrombin IIa (Hideki N., 1995). It has an activation activity of factor XII (Roberto J. 2010). It is generally believed that the wide range of pharmacological mechanisms are relative to bleeding tendency, the side effect of anticoagulant drugs (Bauer, *Hematology*, 2006, (1): 450). The improvement of the selectivity of FGAG for pharmacological targets will be helpful to reduce bleeding tendency.

One approach to improve the selectivity of native FGAG for pharmacological targets is to modify its chemical structure, for example, by peroxide depolymerization of native FGAG (European Patent Publication EP 0408770; Kenichiro Y, 1992), by desulfation or carboxyl reduction (Paulo A S et al., *Thrombosis Research*, 2001, 102: 167), by partial acid hydrolysis (Yutaka Kariya, *Biochem. J.*, 2002, 132: 335; Paulo A S et al., *Thrombosis Research*, 2001, 102: 167), etc. Available information shows that the decrease of molecular weight of native FGAG may affect their pharmacological characteristics, such as reducing the platelet aggregation-inducing activity, weakening ATIII- and HC-II-dependent antithrombin activity (Huizeng Fan, et. al, *Chinese Journal of Biological Chemistry*, 1993, 9 (2): 146; Ma Xi, *Chinese Journal of Hematology*, 1990, 11(5): 241; Paulo A S et al., *J. Biol. Chem.* 1996, 271, 23973; Hideki Nagase et al., *Blood*, 1995, 85 (6):1527). However, simply by depolymerization, it is difficult to obtain an anticoagulant product with both desirable anticoagulant potency and desirable target selectivity. For example, FGAG from *Stichopus japonnicus* can effectively reduce the platelet aggregation-inducing activity only when its weight-average molecular weight (Mw) is as low as approximately 9 kD (Huizeng Fan, et. al, *Chinese Journal of Biological Chemistry*, 1993, 9 (2): 146), while the depolymerization product with Mw of about 12-15 kDa can give proper anticoagulant activity (Nagase et al., *Thromb Haemost*, 1997, 77(2): 399; Kazuhisa M et al., *Kidney Int.*, 2003, 63: 1548; Sheehan et al., *Blood*, 2006, 107(10): 3876; Jinhua Zhao et al., CN101724086A). Both hydrolysis of the fucose branches and partial desulfation can lead to significantly reduction or even disappearance of anticoagulant activity of the FGAG. Carboxyl reduction has relatively less effect on the anticoagulant activity, but bleeding tendency is still significant and its influence on platelet activity is unknown (Paulo A S et al., *Br J. Haematol.*, 1998, 101: 647; Paulo A S et al., *ThrombRes.* 2001, 102: 167).

The present inventors have systematically studied the depolymerization methods of FGAG during the study on the structure-activity relationships of anticoagulant activity of FGAGs from sea cucumbers, including peroxide depolymerization catalyzed by transition metal ions, β-eliminative depolymerization, deacylated and deaminated depolymerization and so on (Jinhua Zhao, et al., CN101735336B; CN103145868A; CN103214591A). The first one can improve the efficiency of the depolymerization reaction and the controllability of the reaction process, the latter two can obtain glycosyl groups with a special reducing or non-reducing end, and significantly improve the quality controllability of the product. Besides, the present inventors have systematically studied the structure modification methods of structure fragment and chemical groups of FGAG (e.g. carboxyl contained in D-β-GlcUA, acetylamino contained in D-β-GalNAc, etc.) and the structure-activity relationships of the structurally modified products (Jikai Liu, et al., CN102558389A; Jinhua Zhao, et al., CN102247401A; Zhao L. et al., *CarbohydrPolym.* 2013, (98):1514; Lian W. et al. *BBA*, 2013, 1830: 4681). However, except non-selective removal of sulfate, all these structural modification methods do not change the degree and position of sulfation on the backbone and branches of FGAG. That is to say, the sulfation patterns of the backbone and branches of FGAG still depend on its native source.

As mentioned above, there can be large difference in the sulfation patterns of the backbone and branches of FGAG from different species. The present inventors have found through the early work that FGAG from *Thelenota ananas* has the advantageous characteristics of weaker platelet activation activity (Jinhua Zhao et al., CN101724086A; Wu et al. *Food Chem.* 2010 (122) 716). However, the sulfation patterns of the L-Fuc branches in FGAG from *Thelenota ananas* are complex (Mingyi W., 2010; Zhao L., 2013; Lian W., 2013), and there is difficulty in the technical issues related to quality analysis, such as the structure confirmation of the depolymerization product, the analysis of chemical structure homogeneity of the product. It has been reported that L-Fuc in the branches of FGAG from *I. badionatus* is mainly Fuc2S4S (~96%) (Chen S G, 2011), which provides convenience for the structure study of FGAG compounds. Since the Fuc2S4S structure is related to the f.XII activation activity of FGAG (Roberto J. 2010), it undoubtedly limits the application value of FGAG with Fuc2S4S as the main composition of the branches.

There were reports on the study of polysaccharide from *Holothuria scabra*, confined to the preliminary study of preparation process and activity of total polysaccharides (Ming Shen et al., *Chinese Journal of Marine Drugs*, 2003, 91(1): 1), the initial analysis of physicochemical property of acid mucopolysaccharide (Jian Chen et al., *Food and Fermentation Industries*, 2006, 32(10): 123) and the investigation of extraction process (Aichu Zheng et al., *Modern Food Science and Technology*, 2007, 23(5):65). The present inventors have found by systematic study on a series of FGAGs from sea cucumbers that, the polysaccharide from *Holothuria scabra* not only includes FGAG, but also includes several acidic fucans (Fucan sulfate) with different structures and degrees of polymerization, and includes neutral polysaccharides with the structure similar to glycogen. Since the several acidic fucans and neutral polysaccharides have the molecular weight similar to FGAG, the polysaccharide composition obtained by the published methods is not expected to be pure FGAG from *Holothuria scabra*.

It is relatively difficult to perform chemical structure analysis of polysaccharides. During the study of the chemical structure of FGAG from *Holothuria scabra* using glycochemistry analysis, enzyme analysis, preparation of special derivatives and spectral analytic techniques, the present inventors have found that FGAG from *Holothuria scabra* has very special chemical structure characteristics, namely that L-Fuc branches are mainly α-L-Fuc3S4S (accounting for more than 75% of all of its branch substituents). NMR spectra and fine chemical structure analysis show that, the repeating structure unit of FGAG from *Holothuria scabra* is more regular than that of FGAG from many other sea cucumbers mentioned above, such as *S. japonicus*, Brazilian sea cucumber *L. grisea*, and *T. ananas*. Obviously, the regularity of this chemical structure is conducive to the realization of its potential application value.

On the other hand, many types of polyanionic substances have f.XII activation (surface activation) activity, such as polyphosphoric acid, RNA fragment, bacterial endotoxin, oversulfated chondroitin (Madman et al., *J Thromb Haemost.* 2010, 8(5):865). Given the data that shows Fuc2S4S structure having higher sulfated fucose branches is related to the f.XII activation activity of FGAG on f.XII (Roberto J., 2010), the loading capacity of negative charges of sulfated groups in the L-Fuc branches is naturally become the key framework features for f.XII activation activity of FGAG. However, the inventors surprisingly further find from a large number of comparative experiment research that, despite that the FGAG from *Holothuria scabra* have higher negative charge loading capacity on the backbone and branch (β-D-GalNAc on the backbone is mainly 4,6-disulfated, and more than 75% of the branch is 3,4-disulfated), the f.XII activation activity of its prototype and depolymerization product is the weakest among the existing FGAGs from sea cucumbers.

When the depolymerization derivatives of FGAG from *Holothuria scabra* are prepared using the techniques established by the present inventors (Jinhua Zhao, et al., CN101735336A; CN 103145868A; CN103214591A), the present inventors surprisingly further find that, compared with the depolymerization products of FGAGs from a variety of other sea cucumbers, the depolymerization product of FGAG from *Holothuria scabra* can remain potent anticoagulant activity at a lower molecular weight (Mw of about 4.5-9 kD). For example, it can show the strongest f.Xase inhibition activity at a Mw of about 5-8 kD, and show the strongest HCII-dependent antithrombin activity at a Mw of about 5 kD. Subsequently, the present inventors have extracted and purified FGAG compounds from *Pearsonothurta graeffei* with similar structure having L-Fuc3S4S as the main branch component. The depolymerization product obtained by the above-mentioned techniques established by the present inventors has the features that it does not affect the activities of f.XII and platelet and its anticoagulant activity is similar to that of the depolymerization product of FGAG from *Holothuria scabra*.

Sulfation patterns of L-Fuc branches rather than simple charge loading capacity significantly affect the pharmacological and pharmacodynamic activity characteristics of FGAG and its derivatives. The FGAG depolymerization product with L-Fuc3S4S as main branch component has a more regular repeating structure unit and has more advantageous anticoagulant pharmacological effect.

Thrombotic diseases continue to be the leading cause of human death, and anticoagulant drugs play an important role in the prevention and clinical treatment of thrombotic diseases. Heparin drugs are the main clinical medication, but there are serious defects like bleeding tendency. It is generally believed that the bleeding tendency is associated with its broader impact on coagulation factors as well as the inhibition of the common coagulation pathway, and the mechanism of f.Xase inhibition and HCII-dependent anti-f.IIa activity may help to reduce the bleeding tendency caused by an anticoagulant active ingredient.

The oligoglycosaminoglycan with L-Fuc3S4S as main branch component from sea cucumbers such as *H. scabra* and *P. graeffei* may have potent anticoagulant activity, and the anticoagulant mechanisms are mainly f.Xase inhibition and HCII-dependent anti-f.IIa activity. The oligoglycosaminoglycan with L-Fuc3S4S as main branch component has a more regular repeating structural unit and has a more advantageous anticoagulant pharmacological characteristics, and thus is potentially applicable for prevention and clinical treatment of thrombotic diseases.

SUMMARY OF THE INVENTION

First, the present invention provides a Fuc3S4S substituted oligoglycosaminoglycan mixture and a pharmaceutically acceptable salt thereof. The Fuc3S4S substituted oligoglycosaminoglycan mixture is a mixture of oligomeric homologous glycosaminoglycan compounds having a structure represented by Formula (I),

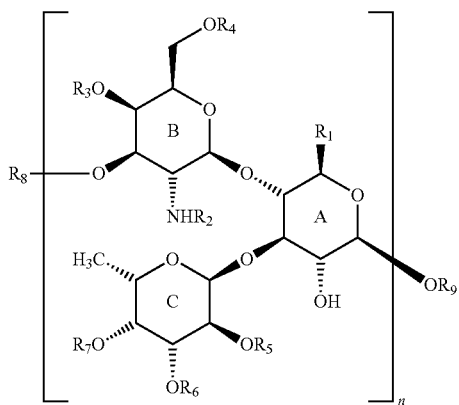

(I)

in Formula (I):

Ring A is β-D-glucuronic acid group or its carboxyl reduction product β-D-glucosyl group (β-D-GlcUA or β-D-Glc). Wherein, $R_1$ is —COO$^-$, —CH$_2$OH, —COR$_{10}$, $R_{10}$ is independently substituted or unsubstituted linear or branched C1-C6 alkyl, C7-C12 aralkyl;

Ring B is substituted β-D-2-amino-2-deoxy-galactosyl. Wherein, $R_2$ is —COCH$_3$ or —H;

$R_3$ and $R_4$ are independently —H or —SO$_3^-$;

Ring C is sulfated α-L-fucosyl (α-L-Fuc). Wherein, $R_5$, $R_6$ and $R_7$ are independently —H or —SO$_3^-$; and based on molar ratio, α-L-fucosyl wherein $R_5$ is —H, $R_6$ and $R_7$ are —SO$_3^-$ (α-L-Fuc3S4S) accounts for not less than 75% of the total α-L-fucosyl;

$R_8$ is the structure represented by Formula (II) or Formula (III)

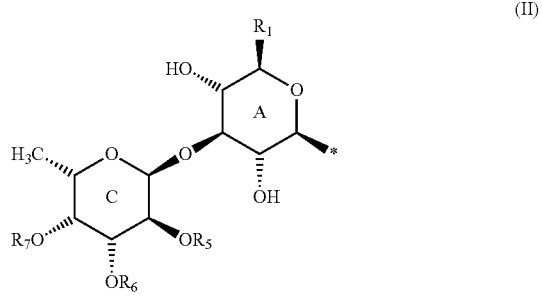

(II)

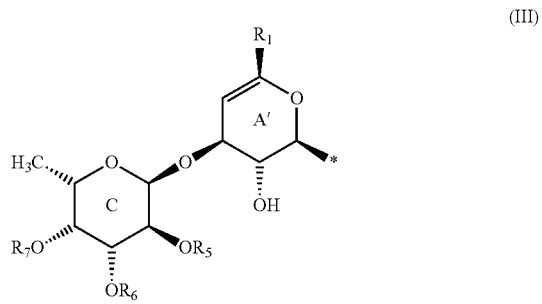

(III)

in Formula (II) and Formula (III):

Ring A is a β-D-glucuronic acid group or β-D-glucosyl (β-D-GlcUA or β-D-Glc),

Ring A' is 4-deoxy-threo-hex-4-enopyranosyluronic acid group (ΔUA), R1 in the formula is defined as above;

Ring C is α-L-fucosyl (α-L-Fuc), wherein, $R_5$, $R_6$ and $R_7$ are defined as above;

$R_9$ is a structure represented by Formula (IV), Formula (V) or Formula (VI):

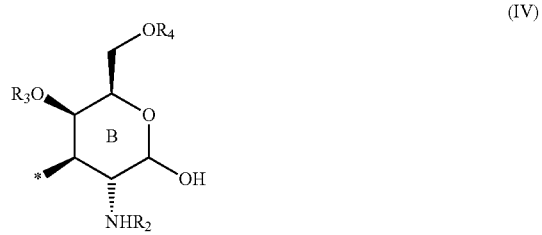

(IV)

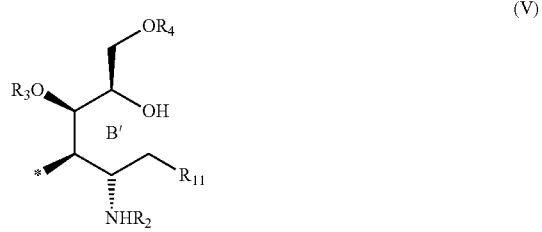

(V)

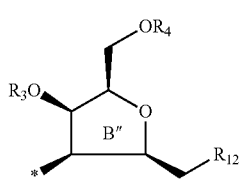
(VI)

in Formula (IV), (V) and (VI):

Ring B is substituted D-2-amino-2-deoxy-galactosyl group (α/β-D-GalNAc), B' is an aldehyde reduction product of substituted 2-amino-2-deoxy-galactose-3-yl: alditol, glycosamine or N-substituted glucosamine thereof, B" is substituted 2,5-anhydrated talosyl (anTal), or alditol, glycosamine or N-substituted glycosamine thereof. Wherein, $R_3$ and $R_4$ are defined as above;

$R_{11}$ is hydroxy, amino, C1-C6 alkylamino, C7-C12 arylamino;

$R_{12}$ is carbonyl, bis-hydroxy, hydroxy, amino, C1-C6 alkylamino, C7-C12 arylamino.

When $R_8$ is the structure of Formula (III), $R_9$ is the structure of Formula (IV) or Formula (V); when $R_9$ is the structure of Formula (VI), $R_8$ is the structure of Formula (II).

n is an integer of 2-20; and based on molar ratio, the compounds which n is 4 to 9 account for not less than 75% of the total compounds;

based on molar ratio, in compounds of Formula (I), α-L-fucose-3,4-disulfated, i.e., Fuc3S4S group, accounts for not less than 75% of the total L-fucosyl;

the oligomeric homologues glycosaminoglycan mixture has a weight average molecular weight (Mw) of 4.5-9 kD, and a polydispersity index (PDI) of less than or equal to 1.6.

In the oligomeric glycosaminoglycan mixture of the present invention, the suitable Mw range is about 4.5-9 kD, and PDI is between about 1-1.6. The person skilled in the art will understand that the mixture of the present invention is composed of a series of compounds of Formula (I) with different degrees of polymerization. It can be seen from the structure of Formula (I), the oligoglycosaminoglycan mixture of the present invention has a characteristic repeating structure unit, which is the part enclosed in bracket of Formula (I), i.e.,

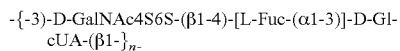

According to the studies on purified structure fragments, when n≥2, compounds of Formula (I) have a certain potency of HCII-dependent antithrombin activity, whereas when n is more than about 20, compounds of Formula (I) may have platelet activating activity. Therefore, during the preparation of the oligoglycosaminoglycan mixture of the present invention, the compounds corresponding to n<2 and n>20 with less or higher polymerization degree will be removed. In a more preferred embodiment, the compounds corresponding to n<3 and n>15 with less or higher polymerization degree will possibly be removed.

According to the activity studies on the related activity of purified structure fragments, when n is an integer of about 4-9, compounds of Formula (I) may have better anticoagulant pharmacological activity characteristic. Generally, in the range of the weight average molecular weight and PDI of oligoglycosaminoglycan mixture defined in the present invention, in the mixture, the proportion of compounds of n being 4 to 9 is not less than 75% of the total compounds, such proportion is generally calculated according to spectrum integral of high performance gel permeation chromatography (HPGPC) of the mixture and molecular weight of structure unit of homologous compounds.

The oligoglycosaminoglycan mixture and a pharmaceutically acceptable salt thereof of the present invention, is generally prepared by chemical depolymerization of Fuc3S4S substituted glycosaminoglycan from sea cucumber. Wherein the Fuc3S4S substituted glycosaminoglycan from sea cucumber has the following features:

(1) the glycosaminoglycan is obtained by extraction from certain specific sea cucumber species, the chemical properties thereof is a glycosaminoglacan derivative having fucose substituent in the branch (i.e., Fucosylated glycosaminoglycan, FGAG);

(2) in the glycosaminoglycan, the monosaccharide composition comprises D-glucuronic acid and D-acetylgalactosamine and L-fucose in a molar ratio of 1:(1±0.3):(1±0.3). Based on molar ratio, the proportion of 3,4-disulfated-L-fucosyl (Fuc3S4S) is not less than 75% in the contained L-fucosyl.

(3) the linkage form of the monosaccharides in the glycosaminoglycan is that, D-glucuronic acid and D-acetylgalactosamine are alternatively linked by β (1-4) glycosidic linkage and β (1-3) glycosidic linkage to form a polysaccharide backbone, and L-fucose residue is linked to the D-glucuronic acid in the backbone by α(1-3) glycosidic bond in the form of branch.

It is known that fucosylated glycosaminoglycans (FGAGs) from different sea cucumber species have certain similarity in basic chemical structure, but may have difference in the sulfation patterns of glycosyl on the backbone and branches. With respect to the Fuc3S4S substituted glycosaminoglycan, the characteristic structural feature is that the sulfation pattern of the fucose branches are mainly 3,4-disulfated. The present invention has found that such structural feature in the FGAG found present in fresh or dried body wall and/or viscera from *Holothuria scabra* or *Pearsonothuria graeffei*. Since the sea cucumber in the world is up to thousands of species, currently the systematic investigation of glycosaminoglycan has been performed only in a small portion of sea cucumber species, thus there may be other sea cucumber species with Fuc3S4S substituted glycosaminoglycan defined in the present invention. Obviously, FGAG extracted from such sea cucumber species can also be used to prepare the Fuc3S4S substituted oligoglycosaminoglycan mixture of the present invention.

As described later, the chemical depolymerization methods for the preparation the oligoglycosaminoglycan mixture of the present invention using the Fuc3S4S substituted glycosaminoglycan from sea cucumber generally include β-eliminative depolymerization, deaminated depolymerization and peroxide depolymerization. The products obtained by different depolymerization methods as well as the modification products thereof after depolymerization may have different terminal structural features. Therefore, the present invention further provides a mixture of oligomeric homologues glycosaminoglycan compounds represented by Formula (VII),

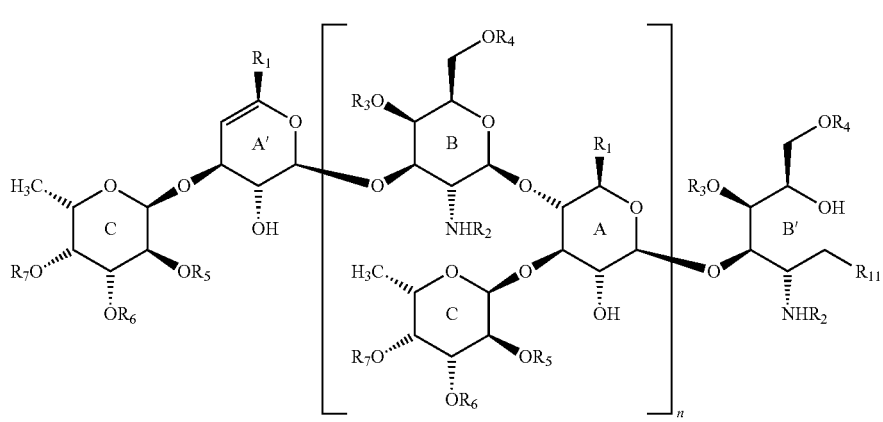

(VII)

in Formula (VII):

chemical structure fragments A, A', B, B', C are defined as above;

$R_1$, $R_2$, $R_3$, $R_4$, $R_5$, $R_6$, $R_7$, $R_{11}$ are defined as above;

n is an integer of 3-15, based on molar ratio, the compounds which n is 4-9 account for not less than 75% of the total compounds;

based on molar ratio, in the compounds of Formula (VII), α-L-fucose-3,4-disulfated, i.e. α-L-Fuc3S4S group, accounts for not less than 75% of the total L-fucosyl;

and the oligomeric homologues glycosaminoglycan mixture has a weight average molecular weight (Mw) of 4.5-9 kD.

The Fuc3S4S substituted oligoglycosaminoglycan mixture of the present invention may also be a mixture of oligomeric homologues glycosaminoglycan compounds represented by Formula (VIII),

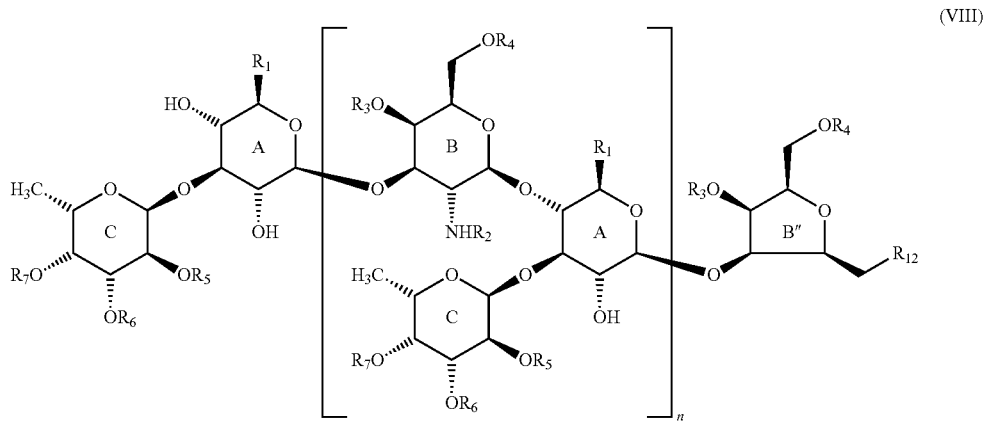

(VIII)

in Formula (VIII):

chemical structure fragments A, B, B", C are defined as above;

$R_1$, $R_2$, $R_3$, $R_4$, $R_5$, $R_6$, $R_7$, $R_{12}$ are defined as above;

n is an integer of 3-15, based on molar ratio, the compounds which n is 4-9 account for not less than 75% of the total compounds;

based on molar ratio, in the compounds of Formula (VIII), α-L-fucose-3,4-disulfated, i.e. α-L-Fuc3S4S group, accounts for not less than 75% of the total L-fucosyl;

and the oligomeric homologues glycosaminoglycan mixture has a weight average molecular weight (Mw) of 4.5-9 kD.

The present inventors have found that when the reductive terminal B" in the compounds of Formula (VIII) is 2,5-anhydrated talose (AnTal), carbonyl at C1 position of the AnTal is prone to bind to one molecule of water to form a diol (AnTal-diol) hydrate structure. Obviously, the hydrate or diol compound is also included within the scope of the present invention.

The Fuc3S4S substituted oligoglycosaminoglycan mixture provided in the present invention may be a mixture of oligomeric homologues glycosaminoglycan compounds represented by Formula (IX),

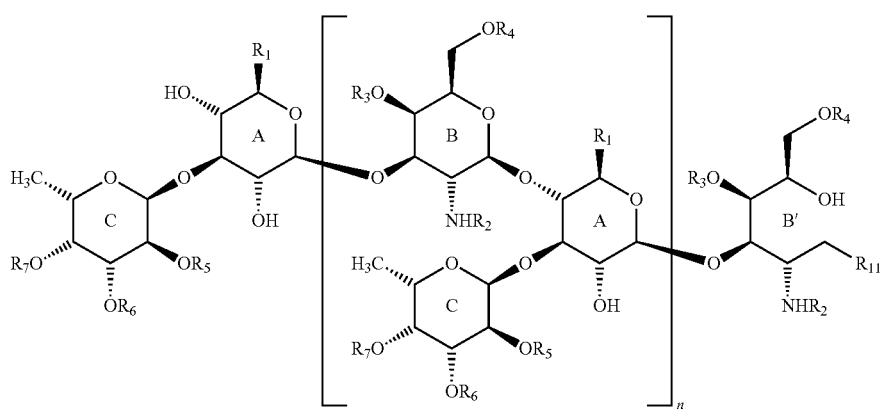

in Formula (IX):

chemical structure fragments A, B, B', C are defined as above;

$R_1$, $R_2$, $R_3$, $R_4$, $R_5$, $R_6$, $R_7$, $R_{11}$ are defined as above;

n is an integer of 3-15, based on molar ratio, the compound that n is 4-9 accounts for not less than 75% of the total compounds;

based on molar ratio, in the compounds of Formula (VIII), α-L-fucose-3,4-disulfated, i.e. α-L-Fuc3S4S group, accounts for not less than 75% of the total L-fucosyl;

and the oligomeric homologues glycosaminoglycan mixture has a weight average molecular weight (Mw) of 4.5-9 kD.

Generally, the pharmaceutically acceptable salt of the present invention may be an alkali metal and/or alkaline earth metal salt. In the present invention, the preferred Fuc3S4S substituted oligoglycosaminoglycan mixture is sodium, potassium or calcium salt thereof.

Further, the present invention also provides a method for preparing the Fuc3S4S substituted oligoglycosaminoglycan mixture and a pharmaceutically acceptable salt thereof, the preparation method comprises the following steps of:

Step 1.

Fresh or dried body wall and/or viscera of sea cucumbers including but not limited to *Holothuria scabra* or *Pearsonothuria graeffei* is used to extract and purify, the polysaccharide composition containing Fuc3S4S substituted glycosaminoglycan.

In the present invention, the extraction steps include chopping, crushing or homogenizing the sea cucumber, using water as an extraction solvent, optionally applying protease treatment and/or inorganic alkaline treatment to obtain the extract containing the Fuc3S4S substituted glycosaminoglycan; the purification step optionally includes ethanol and/or acetone precipitation, ion exchange chromatography, gel filtration chromatography, dialysis and/or ultrafiltration to obtain purified and/or partially purified polysaccharide composition containing Fuc3S4S substituted glycosaminoglycan.

Generally, the polysaccharide composition containing the Fuc3S4S substituted glycosaminoglycan of the present invention refers to, (1) the glycosaminoglycan in the polysaccharide composition having a uniform molecular weight, i.e., showing a single polysaccharide chromatographic peak in gel chromatographic analysis, and having a polydispersity index (PDI) of 1-1.5; (2) the content of Fuc3S4S substituted glycosaminoglycan in the polysaccharide composition not less than about 80%. Wherein, the Fuc3S4S substituted glycosaminoglycan refers to, (i) it is a glycosaminoglycan from sea cucumber, its monosaccharide composition comprises D-glucuronic acid and D-acetylgalactosamine and L-fucose in a molar ratio of 1:(1±0.3):(1±0.3), and (ii) based on molar ratio, in the contained fucosyl, the proportion of 3,4-disulfated-L-fucosyl is not less than 75%.

Currently the Fuc3S4S substituted glycosaminoglycan of the present invention is only found in the body wall and viscera of *Holothuria scabra* or *Pearsonothuria graeffei*. However, in about 1,200 species of sea cucumbers in the world (Chunyun Zhang et al., *Marine Fisheries Research*, 2004, 25 (3): 89), isolation and purification of FGAG has been performed in only a few species of sea cucumbers. Thus, the sea cucumber species containing the Fuc3S4S substituted glycosaminoglycan in line with the definition of the present invention may not be limited to from *Holothuria scabra* and *Pearsonothuria graeffei*. Obviously, those person skilled in the art will easily recognize that, the Fuc3S4S substituted glycosaminoglycan in line with the definition of the present invention, even from other sea cucumber species, also can be used to prepare the Fuc3S4S substituted oligoglycosaminoglycan mixture and pharmaceutically acceptable salt thereof.

Step 2:

The Fuc3S4S substituted glycosaminoglycan in the polysaccharide composition obtained in step 1 is subjected to depolymerization to obtain an oligomeric glycosaminoglycan mixture having a weight-average molecular weight (Mw) of 4.5 kD-9 kD. The depolymerization method is optionally selected from β-eliminative depolymerization (Method 1), deacylated deaminated depolymerization (Method 2) or peroxide depolymerization (Method 3).

Method 1: β-Eliminative Depolymerization:

The method comprises partially converting free carboxyl groups in hexuronic acid contained in the Fuc3S4S substituted glycosaminoglycan in the polysaccharide composition obtained in "step 1" into carboxylate groups by quaternary ammonium salification and esterification, to obtain a carboxylate product of the polysaccharide with carboxylation degree of about 10% to 50%, and remove residual nonacidic polysaccharide impurities in the original polysaccharide composition by this step; and then in non-aqueous solvent with the presence of a base reagent, subjecting the carboxylate product to β-eliminative reaction to obtain a depolymerization product having the target molecular weight, and removing residual fucan impurities in the original polysaccharide composition by molecular weight difference.

The earlier patent filed by the present inventors (CN 201310099800.9) has described the general procedures of FGAG depolymerization by β-eliminative depolymerization. In the "method 1" of the present invention, during the conversation of free carboxyl group in hexuronic acid contained in the Fuc3S4S substituted glycosaminoglycan in the polysaccharide composition obtained in "step 1" into carboxylate group, the polysaccharide composition may be first converted into a quaternary ammonium salt. In general, in this step, quaternary ammonium such as benzethonium chloride can be added into the aqueous solution of the polysaccharide composition of "step 1", and centrifuged to obtain acidic polysaccharide precipitate quaternary ammonium salificated.

It has been found that the polysaccharides from sea cucumber also contain fucan sulfate (FS) and neutral polysaccharide (NP) similar to glycogen. Some types of FS and NP have a molecular weight range similar to FGAG, therefore, during the extraction and purification of FGAG from sea cucumber, it is hard to completely remove the FS and NP contained in the extract by fractional precipitation. In the method of the present invention, during the quaternary ammonium salification of the polysaccharide composition in step 1, the neutral polysaccharide composition cannot be precipitated by quaternary ammonium salt, therefore, after the quaternary ammonium salt precipitate is centrifuged and washed with water, the possible neutral polysaccharide with a molecular weight distribution similar to the Fuc3S4S substituted glycosaminoglycan can be effectively removed.

The acidic polysaccharide precipitate after quaternary ammonium salification is washed and dried, and then dissolved in an aprotic solvent such as N, N-Dimethylformamide (DMF), and reacted with stoichiometric halogenated hydrocarbon, to obtain a carboxylate derivative of the FGAG quaternary ammonium salt. The alkyl in the halogenated hydrocarbon includes but not limited to C1-C6 straight or branched chain, saturated or unsaturated, substituted or unsubstituted aliphatic alkyl, and substituted or unsubstituted C7-C12 aromatic hydrocarbon. The preferred halogenated hydrocarbon of the present invention includes benzyl bromide and benzyl chloride.

In general, the weight-average molecular weight of the target product of the present invention is within the range of 4.5-9 kD. In view of the actual reaction efficiency of β-eliminative reaction, the degree of esterification of the FGAG carboxylate derivative is generally selected in the range of 10%-50%. The degree of esterification of the carboxylate derivatives may be calculated according to $^1$H NMR spectrum.

The present inventors have found that, the FGAG carboxylate derivative is easily hydrolyzed in water or aqueous solvent under alkaline condition. Thus, in the β-eliminative reaction of the Fuc3S4S substituted glycosaminoglycan, the carboxylate derivative is reacted in a non-aqueous solvent in the presence of an alkaline reagent, to obtain the depolymerization product. In the present invention, the preferred non-aqueous solvent is ethanol, and the preferred alkaline reagent is ethanol sodium.

β-elimination depolymerization of the FGAG carboxylate derivative can be performed in the presence of an alkaline reagent, whereas FS is not depolymerized due to the absence of hexuronic acid. The result is that, after β-eliminative treatment, the original FGAG and FS with similar molecular weight in the polysaccharide differs distinctly in the molecular weight range. By further gel filtration, ultrafiltration and/or dialysis treatment, residual FS compositions in the depolymerization product of FGAG can be easily removed. Therefore, by the β-eliminative reaction, besides the Fuc3S4S substituted oligoglycosaminoglycan of the present invention can be obtained, the residual FS polysaccharide compositions in the original polysaccharide composition can be effectively removed and the purity of the product of the present invention is improved.

The oligomeric homologues glycosaminoglycan mixture of the present invention can be obtained by purification of the β-eliminative depolymerization product by the above method. In the homologues glycosaminoglycan mixture, some glucuronic acid is still present in the form of carboxylate. The ester group of the carboxylate is C1-C6 alkyl or C7-C12 aralkyl. The carboxylate-containing oligomeric homologues glycosaminoglycan mixture may optionally be hydrolyzed in water or aqueous solvent under alkaline condition, to obtain oligomeric homologues glycosaminoglycan containing no carboxylate.

Further, the carboxyl groups on glucuronic acid of the oligomeric homologues glycosaminoglycan may be reduced in the presence of carbodiimide compounds by a reducing agent such as sodium borohydride to the corresponding hexose group, i.e. D-glucosyl.

The obtained oligomeric homologues glycosaminoglycan may be optionally subjected to reduction treatment at reducing terminal, and the reducing terminal D-2-acetylamino-2-deoxy-galactosyl is converted into its corresponding alditol, glycosamine or N-substituted glucosamine. The method for converting the reducing sugar at the reducing terminal of polysaccharide and/or oligosaccharide into the corresponding alditol, glycosamine or N-substituted glucosamine is well known to those skilled in the art, for example, treatment under alkaline conditions with sodium borohydride or cyanoborohydride sodium can easily reduce the reducing sugar into alditol, treatment with ammonium hydrogen carbonate and cyanoborohydride sodium can reduce the reducing sugar into the corresponding glucosamine. In the presence of an organic amine, the reducing terminal can be reductively aminated, with the reaction that the organic amine is reacted with C1 aldehyde group of the terminal glycosyl to produce a Schiff alkaline, which is reduced to a secondary amine called the N substituted glucosamine in the presence of a reducing agent.

The steps for preparation of desired oligomeric homologues glycosaminoglycan mixture by β-eliminative depolymerization of "Step 2" of the present invention can be summarized as follows:

Polysaccharides containing Fuc3S4S substituted glycosaminoglycan (polysaccharide extracted from sea cucumber)
  ↓ quaternary ammonium salinization, and removal of neutral polysaccharide polysaccharides containing quaternary ammonium salt of Fuc3S4S substituted glycosaminoglycan
  ↓ carboxyl esterification reaction (in an aprotic solvent, reacted with halogenated hydrocarbon)
polysaccharides containing partial carboxylated quaternary ammonium salt of Fuc3S4S substituted glycosaminoglycan ↓ β-eliminative reaction (non-aqueous solvent, treatment with a strong alkaline)
↓ purification (gel chromatography, ultrafiltration and/or dialysis)
partially carboxylated Fuc3 S4S substituted oligoglycosaminoglycans
  ↓ carboxylate hydrolysis (in an aqueous solution, treatment with a alkaline) (Optionally)
Fuc3S4S substituted oligoglycosaminoglycan
  ↓ carboxyl reduction (in an aqueous solvent, treatment with carbodiimide/a reducing agent) (Optionally)
Carboxyl-reducing oligosaccharides glycosaminoglycans
  ↓ terminal reduction (in an aqueous solvent, treatment with a reducing agent under alkaline conditions) (Optionally) or
  ↓ Terminal reductive amination (treatment with ammonium bicarbonate/organic amine and a reducing agent)
oligoglycosaminoglycan with aminohexitol or the corresponding glucosamine or substituted glucosamine as terminal Method 2. Deacylated Deaminated Depolymerization.

The deacylated deaminated depolymerization process comprises: treating the polysaccharide composition obtained in "step 1" with hydrazine in the presence or absence of hydrazine sulfate, allowing 10% to 35% of D-acetylamine galactosyl in the Fuc3S4S substituted glycosaminoglycan to perform deacetylation reaction, to obtain partial deacetylated product. then treating the obtained partial deacetylated product with nitrite to perform deamination and depolymerization, to obtain the oligomeric homologues glycosaminoglycan mixture with 2, 5-anhydrated talosyl as reducing terminal.

Another patent application of the present inventors (CN 201310127447.0) has described the general procedures for FGAG depolymerization by deacetylated deaminated depolymerization. Generally, the partial deacylation reaction of "Method 2" is to dissolve the polysaccharide composition containing Fuc3S4S substituted oligoglycosaminoglycan obtained in "Step 1" in anhydrous or aqueous hydrazine. Into the resulting hydrazine solution of the polysaccharide, a small amount of hydrazine sulfate or hydrazine hydrochloride as reaction catalyst is added, or a small amount of sulfuric acid or hydrochloric acid as reaction catalyst is added, followed by reacting under heated (for example, 60° C.-110° C.) and stirring conditions, allowing the deacetylation degree of the Fuc3S4S substituted glycosaminoglycan in the polysaccharide composition to reach about 10% to 35%. The deacetylation reaction is preferably carried out under a nitrogen atmosphere. The degree of deacetylation of the Fuc3S4S substituted glycosaminoglycan can be measured by $^1$H NMR spectrum.

Deaminated depolymerization of the deacetylation product is generally carried out in ice bath at room temperature, i.e., dissolving the polysaccharide composition containing Fuc3S4S substituted oligoglycosaminoglycan in water, adding nitrite solution to adjust the pH of the solution to about 2-5, or directly dissolving the polysaccharide composition containing Fuc3S4S substituted oligoglycosaminoglycan in nitrite solution with pH of about 2-5. In general, deaminated depolymerization of the deacetylation product of the Fuc3S4S substituted glycosaminoglycan is carried out rapidly and completely, the reaction is completed in 5-60 min. In order to avoid the removal of fucose branches under acidic conditions, one the reaction is completed, generally an alkaline solution such as sodium carbonate is immediately added to adjust pH to about 8-9 to terminate the reaction.

As previously described, besides FGAG, the polysaccharides from *Holothuria scabra* and *Pearsonothuria graeffei* also contain FS and NP polysaccharides. Since some types of FS and NP have a molecular weight range similar to FGAG, during the extraction and purification process of FGAG from sea cucumber, it is difficult to remove the FS and NP contained in the extract completely by fractional precipitation. When the polysaccharide composition containing Fuc3S4S substituted glycosaminoglycan is depolymerized by deacylated deaminated depolymerization, FS and NP are hardly depolymerized during the treatment steps of "Method 2" due to the absence of hexosamine. Therefore, after the treatment by steps of Method 2, the molecular weights of FS and NP in the polysaccharide composition obtained in "Step 1", which are similar to that of the Fuc3S4S substituted glycosaminoglycan, are basically not changed, whereas the molecular weight of the Fuc3S4S substituted glycosaminoglycan is significantly decreased. Based on the significant difference in molecular weight distribution, the residual FS and NP polysaccharides in the polysaccharide composition can be easily removed by gel chromatography, ultrafiltration and/or dialysis.

Similarly, the oligomeric homologous glycosaminoglycans can be optionally subjected to carboxyl reduction treatment to reduce the D-glucuronic acid into D-glucosyl, or optionally subjected to reduction at reducing terminal to convert the 2, 5-dehydrated talosyl at reducing terminal into its corresponding alditol, glucosamine or N-substituted glucosamine. The method for reducing the carboxyl and reducing terminal glucosyl of the oligomeric homologous glycosaminoglycans is the same as described in Method 1.

The steps of preparation of the desired oligomeric homologous glycosaminoglycan mixture by the deacylated deaminated depolymerization described in "Step 2" of the present invention can be summarized as follows:
polysaccharides extracted from sea cucumber containing the Fuc3S4S substituted glycosaminoglycan
  ↓ hydrazine hydrolysis (hydrazine, optionally with sulfuric acid (hydrazine sulfate) or hydrochloric acid (hydrazine hydrochloride) as a catalyst)
polysaccharides containing partial deacylated Fuc3S4S substituted glycosaminoglycan
  ↓ deaminated depolymerization (in an aqueous solvent, treatment with nitrous acid)
  ↓ purification (gel chromatography, ultrafiltration and/or dialysis)
Fuc3S4S substituted oligoglycosaminoglycan
  ↓ terminal reduction (in an aqueous solution, treatment with a reducing agent under alkaline condition) (optionally)
  ↓ terminal reductive amination (treatment with ammonium bicarbonate/organic amine and a reducing agent)
oligoglycosaminoglycan with aminohexitol or the corresponding glucosamine, or substituted glucosamine as terminal Methods 3.

Peroxide depolymerization method. In the presence of copper ions, treating the polysaccharide composition obtained in "Step 1" with $H_2O_2$ of a concentration of 3%-10%, to obtain the oligomeric homologues glycosaminoglycan mixture having the target molecular weight range.

The general procedures of peroxide depolymerization can be seen in the patent (CN101735336B) of the present inventors. The polysaccharide composition containing Fuc3S4S substituted glycosaminoglycan, also contains FS and NP polysaccharides having a molecular weight range similar to FGAG. The above mentioned β-eliminative depolymerization and deacylated deaminated depolymerization have strict glycosidic linkage selectivity, and can depolymerize the FGAG containing hexuronic acid and hexosamine, but cannot depolymerize FS and NP polysaccharides. On the contrary, peroxide polymerization have certain depolymerization impact on all of FGAG, FS and NP, although the depolymerization efficiency may be different. Therefore there is certain difficulty to remove FS and NP polysaccharides effectively by the difference in the molecular weight of the depolymerization products. In general, the product is still required to be further processed by other purification techniques such as anion exchange resin chromatography.

Similarly, the oligomeric homologous glycosaminoglycan can be optionally subjected to carboxyl reduction treatment, reducing the D-glucuronic acid into D-glucosyl; and optionally subjected to reduction at reducing terminal, converting the D-2-acetylamino-2-deoxy-galactosyl at reducing terminal into its corresponding alditol, glucosamine or N-substituted glucosamine. The method for reducing the carboxyl and reducing terminal glucosyl of the oligomeric homologous glycosaminoglycan is the same as described in Example 1.

The depolymerization product and the terminal reductive depolymerization product prepared by any one of Method 1 to Method 3 may be optionally purified by well-known methods in the art such as ethanol and/or acetone precipitation, ion exchange chromatography, gel filtration chromatography, dialysis and/or ultrafiltration, followed by vacuum drying and/or freeze drying to obtain solid oligomeric Fuc3S4S substituted homologous glycosaminoglycan mixture.

Obviously, in the methods of "Step 2", "Method 1" is suitable for preparing the oligoglycosaminoglycan mixture represented as Formula (VII), "Method 2" is suitable for preparing the oligoglycosaminoglycan mixture represented as Formula (VIII), "Method 3" is suitable for preparing the oligoglycosaminoglycan mixture represented as Formula (IX). All the glycosaminoglycan mixture represented as Formula (VII), Formula (VIII) and Formula (IX) are within the scope of the oligomeric Fuc3S4S substituted glycosaminoglycan mixture represented as Formula (I). Generally, "Method 1" or "Method 2" in "Step 2" is preferably used to prepare the oligomeric Fuc3S4S substituted glycosaminoglycan mixture of the present invention.

Therefore, the invention further provides a preparation method of the oligomeric Fuc3S4S substituted glycosaminoglycan mixture represented by Formula (VII) and its pharmaceutically acceptable salt. In the preparation method, the polysaccharide composition containing Fuc3S4S substituted glycosaminoglycan obtained in "Step 1" is depolymerized by the β-eliminative depolymerization of "Method 1" in "Step 2". And the esterification reaction step of "Method 1" is converting the Fuc3S4S substituted glycosaminoglycan in the polysaccharide component into its quaternary ammonium salt, followed by reacting it with a halogenated hydrocarbon or a halogenated aromatic hydrocarbon in an aprotic solvent system to obtain the carboxylate product of the glycosaminoglycan with an esterification degree of about 10%-50%; in the step of β-eliminative reaction, the non-aqueous solvent is selected from the group consisting of ethanol, methanol, dimethylformamide, dimethylsulfoxide, $CH_2Cl_2$ and $CHCl_3$ or a mixture thereof, the alkaline reagent is optionally selected from the group consisting of NaOH, KOH, C1-C4 alcohol sodium, ethylenediamine, tri-n-butylamine and 4-dimethylamino pyridine or a mixture thereof. The depolymerization product prepared by "Method 1" is optionally subjected to carboxylate hydrolysis, optionally subjected to carboxy reduction reaction, and optionally subjected to terminal reduction treatment, and the reducing terminal D-2-acetylamino-2-deoxy-galactosyl is converted into its corresponding alditol, glucosamine or N-substituted glucosamine. The depolymerization product and the terminal reductive depolymerization product is optionally purified by ethanol and/or acetone precipitation, ion exchange chromatography, gel filtration chromatography, dialysis and/or ultrafiltration, and subjected to vacuum drying and/or freeze drying to obtain solid Fuc3S4S substituted oligomeric homologues glycosaminoglycan mixture.

Similarly, the present invention further provides a preparation method for the Fuc3S4S substituted oligoglycosaminoglycan mixture represented as Figure (VIII) and its pharmaceutically acceptable salt. In the preparation method, the polysaccharide containing Fuc3S4S substituted glycosaminoglycan obtained in "Step 1" is depolymerized by the deacylated deamination of "Method 2" in "Step 2", and the hydrazine treatment step of "Method 2" is dissolving the glycosaminoglycan mixture in anhydrous hydrazine or hydrazine hydrate solution, reacting in the presence or absence of hydrazine sulfate. The nitrite treatment in "Method 2" is under the temperature conditions of ice bath to room temperature, adding the partial deacetylated product into nitrite solution with pH 2-5 and reacting for 5-60 min, adjusting the solution to alkaline pH to terminate the reaction. The depolymerization product prepared in "Method 2" is subjected to carboxyl reduction to reduce the glucuronic acid to glucosyl; and optionally subjected to terminal reduction treatment, to convert the reducing terminal 2, 5-anhydrated talosyl into its corresponding alditol, glucosamine or N-substituted glucosamine. The depolymerization product and the terminal reductive depolymerization product is optionally purified by precipitation, ion exchange chromatography, gel filtration chromatography, dialysis and/or ultrafiltration, and subjected to vacuum drying and/or freeze drying to obtain solid Fuc3S4S substituted oligomeric homologues glycosaminoglycan mixture.

The present inventors have found by comparative study on FGAGs from various sea cucumber species that due to the differences in structure, FGAGs from different species have certain differences in the f.XII and platelet activation activity, wherein, FGAG from *Holothuria scabra* has relative low or the lowest f.XII and platelet activation activity, but has stronger anticoagulant activity. The results of the present invention show that, the difference in anticoagulant and procoagulant activity of FGAGs from different sea cucumbers is not simply and directly related to the sulfate content of the polysaccharide, and FGAG from *Holothuria scabra* has special and advantageous anticoagulant activity feature, related to its special sulfate substitution patterns, especially related to the sulfation patterns of the main Fuc3S4S branches.

In the comparison studies on the activities of FGAG depolymerization product with series of molecular weights from sea cucumber, the present inventors have surprisingly found that, compared with the previously reported effect of weight-average molecular weight (Mw) on the anticoagulant activity of FGAG depolymerization products from *Thelenota ananas* (Jinhua Zhao, et al., CN101724086A), Mw has very different effect on the anticoagulant activity of FGAG depolymerization product from *Holothuria scabra*.

In the range of Mw from about 6.5 kD to about 65 kD, if Mw is less than about 10 kD, inhibition activity of the FGAG depolymerization product from *Thelenota ananas* on factor X enzyme (f.Xase) can be significantly decreased with the decrease of Mw. In the range of Mw from 6.5 kD to about 65 kD, its heparin cofactor II (HCII)-dependent antithrombin (f.IIa) activity is basically stable, except slightly increased at molecular weight of about 10-12 kD.

The present invention has found by study that, in the Mw range from about 3.5 kD to about 65 kD, FGAG depolymerization product from *Holothuria scabra* still exhibits the strongest f.Xase inhibition activity when with Mw of about 5-8 kD, and the HCII-dependent anti-f.IIa activity is increased with the decrease of the molecular weight, and the strongest activity is exhibited with Mw of 5 kD.

Similar to the depolymerization product of FGAG from *Thelenota ananas*, the activity of depolymerization product of FGAG from *Holothuria scabra* for doubling human standard plasma thromboplastin time (APTT) is decreased with the decrease of Mw. However, if Mw is less than about 10 kD, the drug concentration of depolymerization product of FGAG from *Thelenota ananas* required to double APTT must be higher than 6 g/ml. If the Mw is as low as about 6 kD, the drug concentration of depolymerization product of FGAG from *Holothuria scabra* required to double APTT is still less than 6 g/ml.

Obviously, compared with FGAG depolymerization product from sea cucumbers such as *Thelenota ananas*, the FGAG depolymerization product from *Holothuria scabra* has better anticoagulant pharmacological characteristics. In other words, FGAG depolymerization product from sea cucumber with Fuc3S4S as main fucose branch has better anticoagulant pharmacological characteristics. Since the backbones have similar structure type, i.e., hexosamine in the backbones of FGAGs from *Thelenota Ananas* and *Holothuria scabra* is mainly β-D-GlcNAc4S6S, the pharmacological activity characteristics the depolymerization product are obviously related to the special pattern of fucose branch substitutions. And, FGAG from *Pearsonothuria graeffei* has the similar structure to FGAG from *Holothuria scabra* and has Fuc3S4S as main fucose branch substitution. The depolymerization product of FGAG from *Pearsonothuria graeffei* has advantageous characteristics of anticoagulant pharmacological pharmacodynamic activity, similar to the depolymerization product of FGAG from *Holothuria scabra*. This further demonstrates that, the structure characteristics of the branched Fuc3S4S fucosyl have significant effect on the advantageous anticoagulant activity characteristics of FGAG depolymerization product.

Thrombotic diseases continue to be the leading cause of human death, and anticoagulant drugs play an important role in the prevention and clinical treatment of thrombotic diseases. Although heparin and low molecular weight heparins are still the main clinical medication, they have serious bleeding tendency. The main anticlotting mechanisms of heparin and low molecular weight heparins are antithrombin III (ATIII)-dependent anticoagulant f.IIa and anti-activated factor X (f.Xa) activity. Available data show that the mechanisms of f.Xase inhibition and HCII-dependent anti-f.IIa activity are helpful to reduce the bleeding tendency caused by an anticoagulant active ingredient. Therefore, FGAG depolymerization product with Fuc3S4S as main branch from sea cucumber such as *Holothuria scabra* is potentially applicable for the prevention and clinical treatment of thrombotic diseases.

Thus, the present invention provides a pharmaceutical composition comprising the Fuc3S4S substituted oligoglycosaminoglycan mixture and a pharmaceutically acceptable salt thereof, characterized in that, the pharmaceutical composition comprises an anti-clotting effective amount of the oligoglycosaminoglycan mixture or a pharmaceutically acceptable salt thereof, and a pharmaceutical excipient.

The biologically active ingredient contained in the pharmaceutical composition of the present invention is an oligosaccharide compound, due to the limited bioavailability of its parenteral administration, in general, its suitable systemic administration route is preferably parenteral administration route, e.g., intravenous administration, intramuscular injection, subcutaneous injection.

The preparations corresponding to the systemic administration route may include aqueous solution for injection, freeze-dried powder for injection that is prepared into aqueous solution before use. Thus, the pharmaceutical composition of the present invention is preferably in a dosage form of an aqueous solution for injection or freeze-dried powder for injection.

Since the oligoglycosaminoglycan mixture of the present invention generally has good water solubility, during the preparation of its aqueous solution, preferably no auxiliary solvent and/or surfactant is contained in the prescription. The selectable pharmaceutical excipient may include an inorganic salt such as sodium chloride, a buffer salt such as phosphate, for regulation of osmotic pressure and/or pH.

For the freeze-dried powder for injection that is prepared into solution before use, in addition to the pharmaceutically acceptable inorganic salt and/or buffer salt for regulation of osmotic pressure and/or pH, the pharmaceutically acceptable excipient that is helpful in the preparation process such as mannose may also be used.

The pharmaceutical composition of the present invention, an effective anticoagulant amount of the oligoglycosaminoglycan mixture refers to the significant and appropriate inhibition of endogenous clotting activity in the user after single and continuous administration. In general, it refers to the ability to allow the plasma APTT of the user to be prolonged by about 0.5-1.5 times. Thus, with respect to the preparation for a single dose, the content of the oligoglycosaminoglycan mixture of the present invention in a dose unit may be between about 20 mg and about 100 mg in a dose unit; and with respect to the preparation for intravenous infusion, it can be properly adjusted according to the actual situation.

Since the Fuc3S4S substituted oligoglycosaminoglycan mixture has antithrombotic and anticoagulant activity, and has clinical application value for prevention and treatment of thrombotic diseases, the present invention also provides a use of the Fuc3S4S substituted oligoglycosaminoglycan derivative in preparing medicines for the treatment and/or prevention of thrombotic diseases. The thrombotic diseases include, but are not limited to intravenous thrombosis, arterial thrombosis, ischemic heart disease, and ischemic cerebrovascular disease.

Further, the present invention also provides a use of the pharmaceutical composition containing Fuc3S4S substituted oligoglycosaminoglycan in preparing medicines for the treatment and/or prevention of thrombotic diseases. The thrombotic diseases include, but are not limited to intravenous thrombosis, arterial thrombosis, ischemic heart disease, and ischemic cerebrovascular disease.

DESCRIPTION OF THE INVENTION

FIG. 1. HPGPC spectrum of polysaccharide composition containing Fuc3S4S substituted glycosaminoglycan from *Holothuria scabra*

Figure 2:
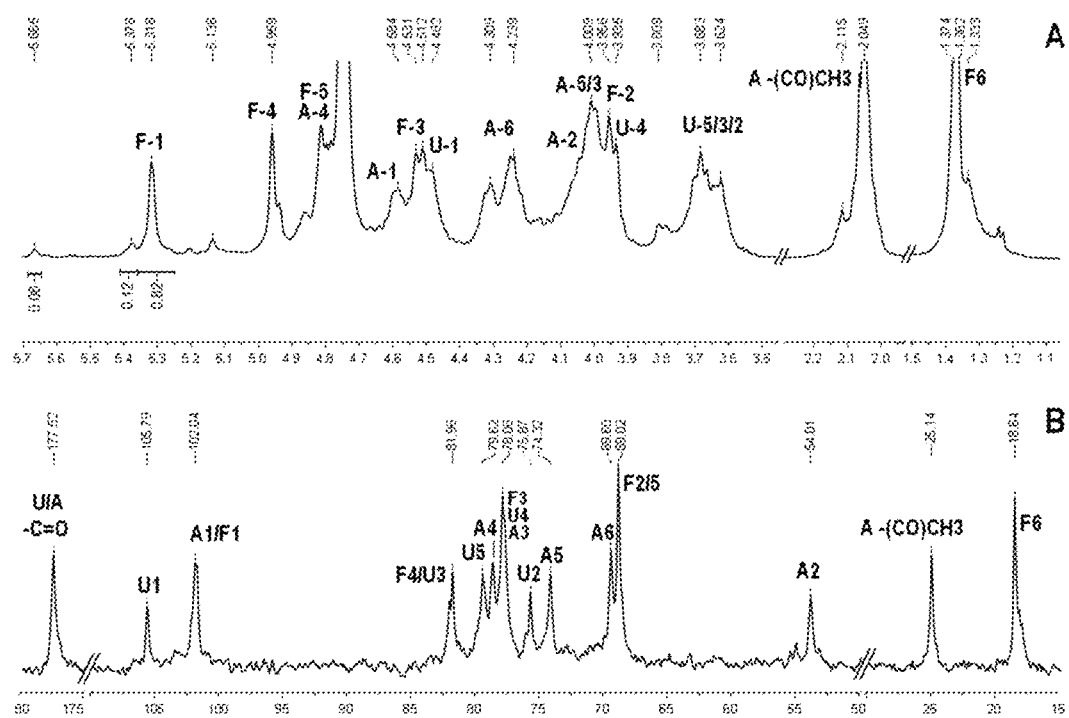

FIG. 2. $^1H/^{13}C$ NMR spectra of Fuc3S4S substituted oligoglycosaminoglycan mixture dHSG-1

Figure 3:
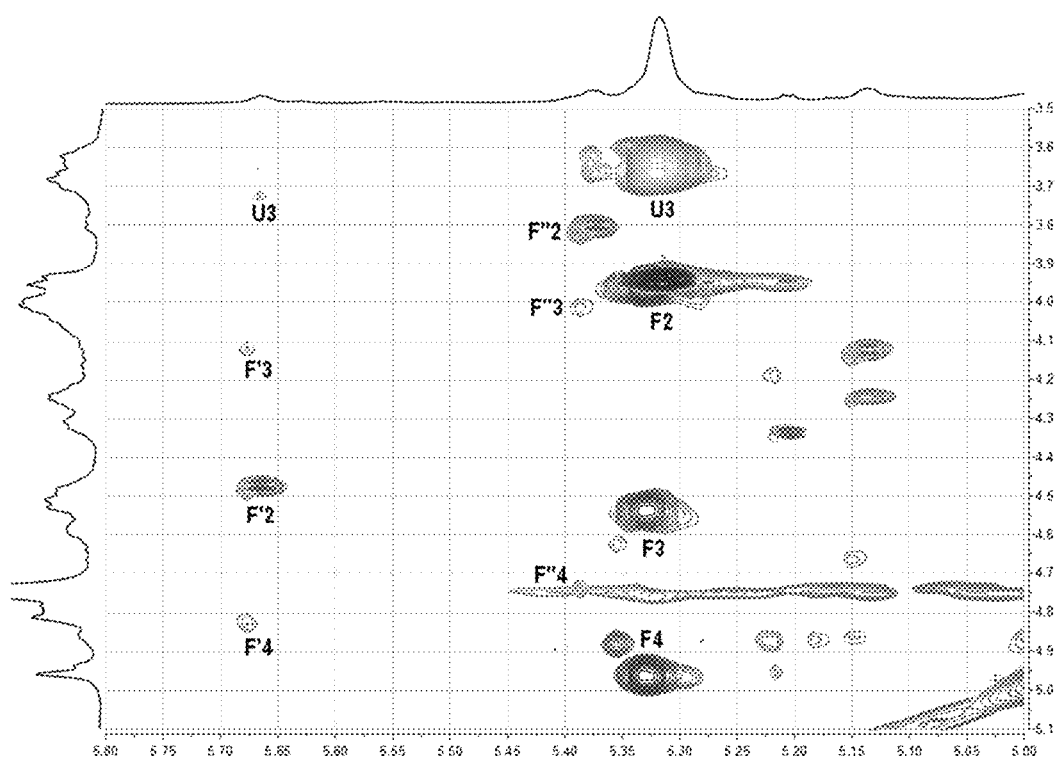

FIG. 3. (partial) superposition of $^1$H-$^1$H COSY, ROESY and TOCSY spectra of dHSG-1

Figure 4:
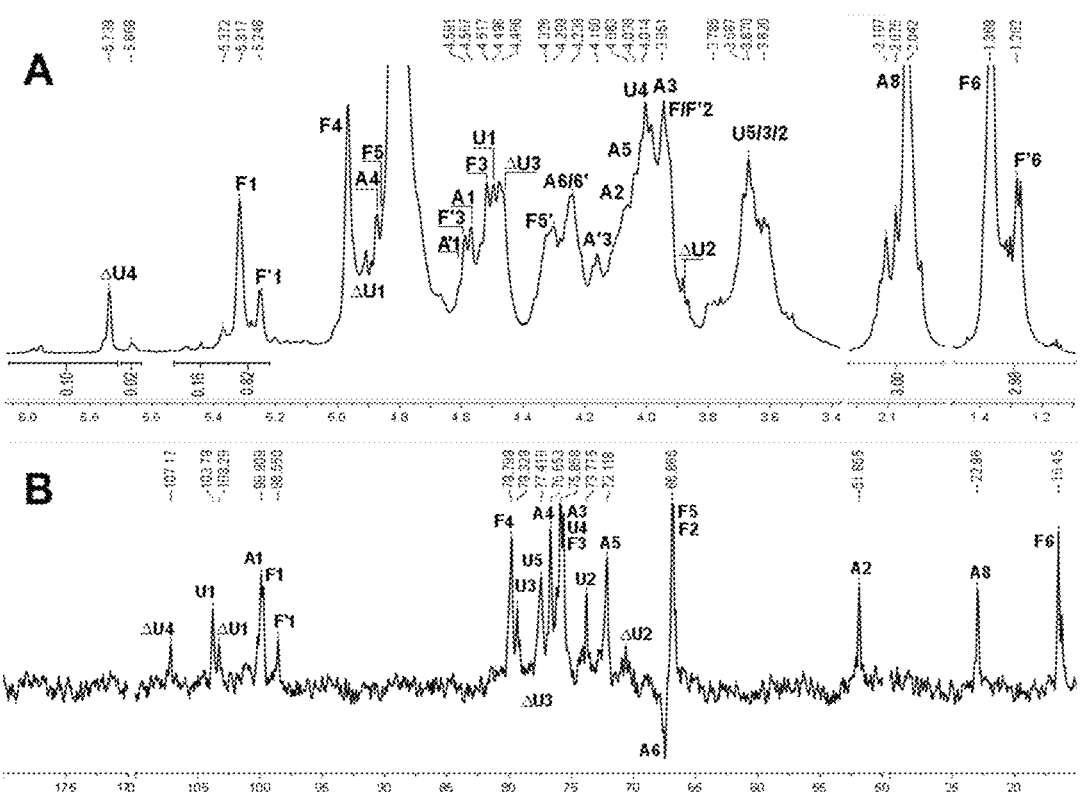

FIG. 4. $^1$H/$^{13}$C NMR spectra of Fuc3S4S substituted oligoglycosaminoglycan mixture dHSG-3

Figure 5:
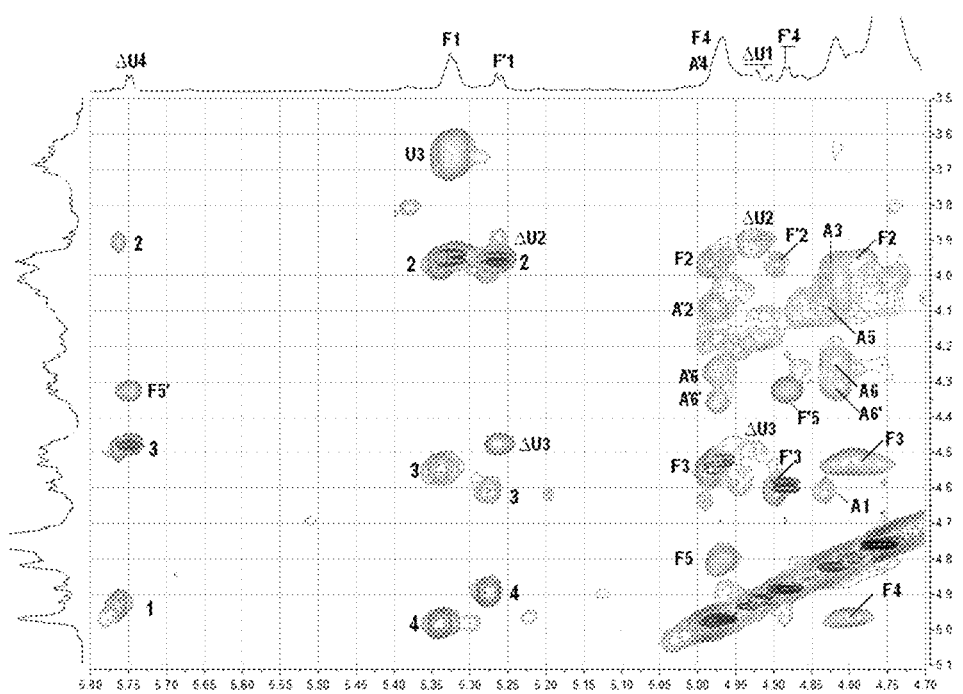

FIG. 5. (partial) superposition of $^1$H-$^1$H COSY, ROESY and TOCSY spectra of dHSG-3

Figure 6:
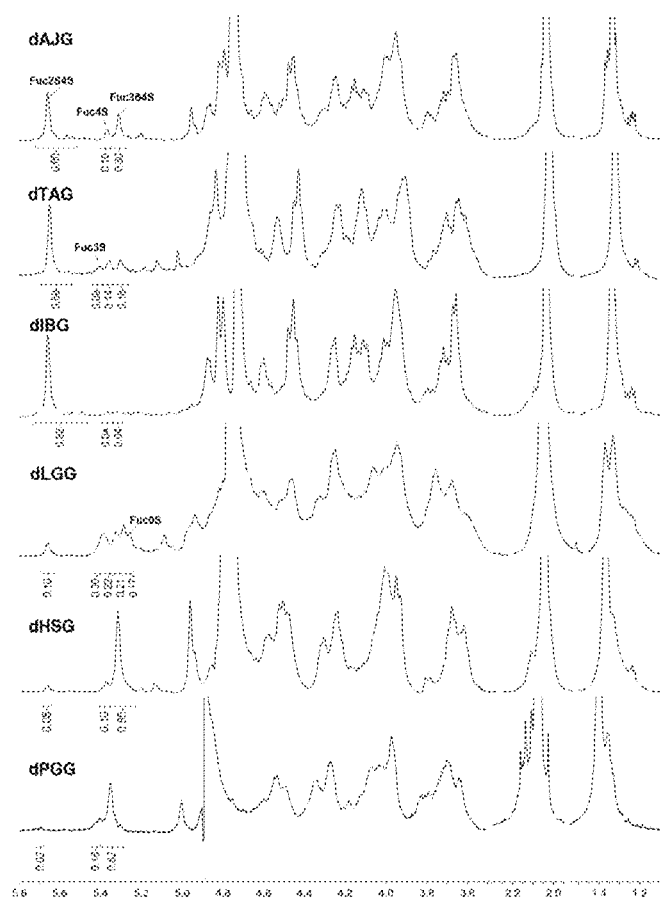

FIG. 6. $^1$H-NMR spectra of dFGAGs from different sea cucumbers

Figure 7:
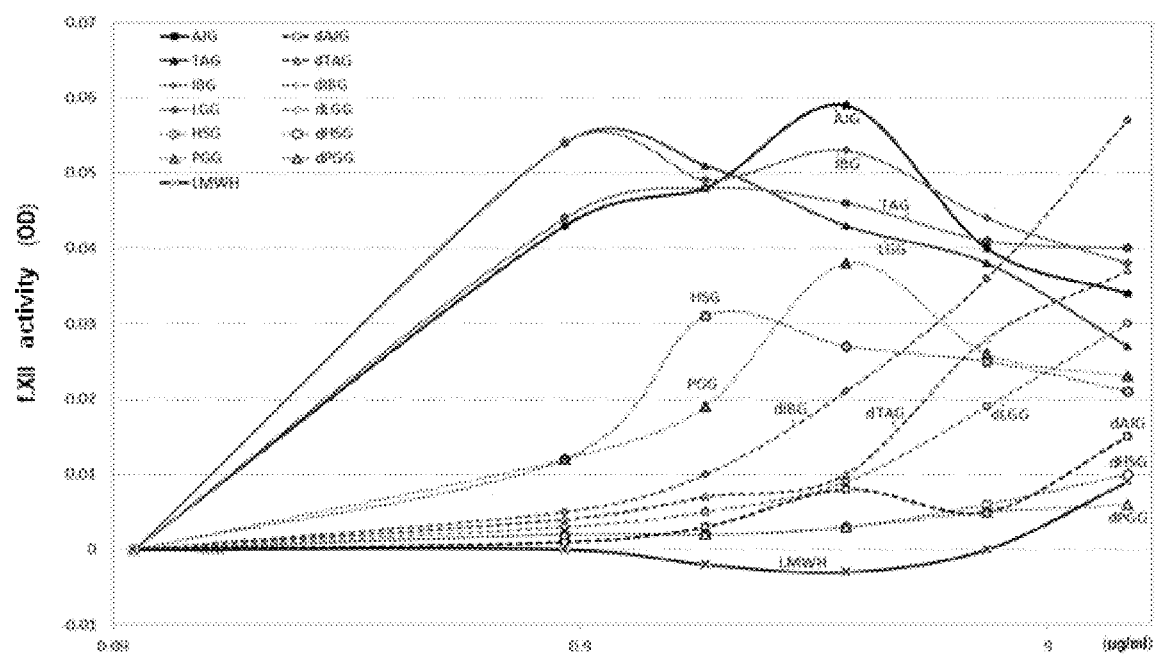

FIG. 7. Effect of FGAG and dFGAG from different species on f.XII activity

Figure 8:
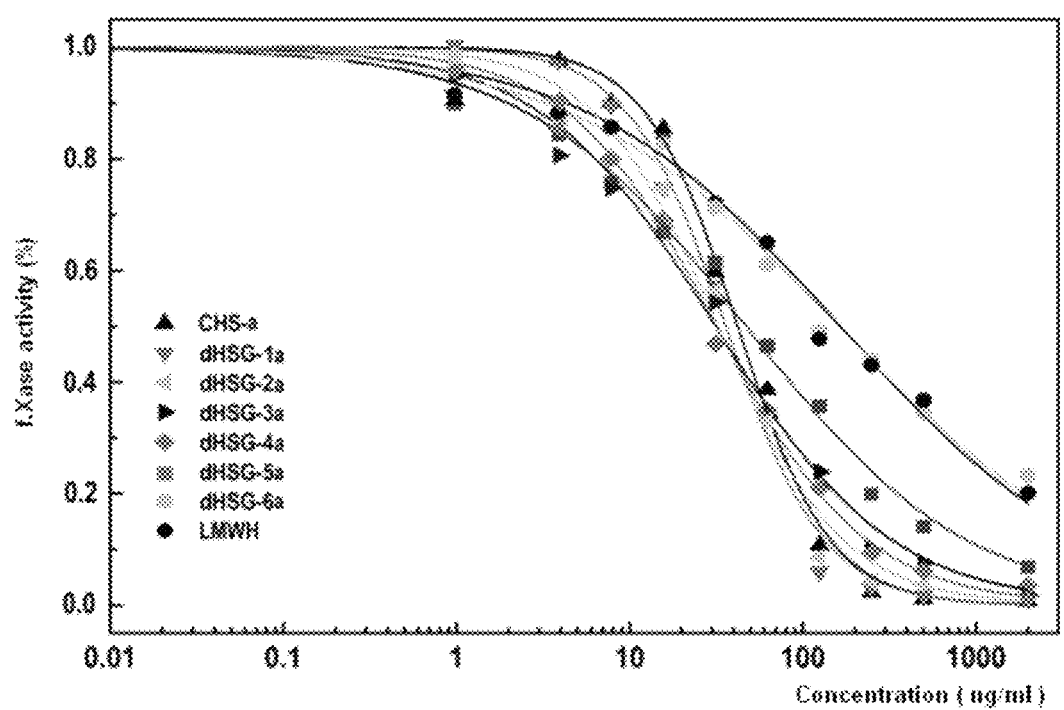

FIG. 8. Effect of HSG and dHSG with series of molecular weights on f.Xase activity

DETAILED DESCRIPTION OF THE INVENTION

The present invention is described in detail below with reference to certain specific examples, but these specific examples do not limit the scope claimed in the present invention in any way.

Example 1

Extraction and Purification of Polysaccharide Composition Containing Fuc3S4S Substituted Glycosaminoglycans from *Holothuria scabra* (HSG-1, HSG-1, HSG-3)

1.1 Materials
Raw Material:
dried *Holothuria scabra*, commercially available.
Reagents:
papain, 8×10$^5$ U/g, Nanning Pangbo Biological Engineering Co., LTD (Guangxi). NaOH, KCOCH$_3$, H$_2$O$_2$ and ethanol and others were commercially available analytical reagents.
1.2 Extraction and Purification
Extraction:
1000 g of dried *Holothuria scabra* was mechanically sliced, grounded and placed in a round-bottomed flask. 10 L of water was added to soak it overnight. The water bath was heated to 50° C., and 5 g of papain was added and fully mixed, and stirred at 50° C. for 6 hr for digestion. Subsequently, solid sodium hydroxide was added to a concentration of about 0.5 M, and alkaline hydrolysis was performed at 60° C. for 2 hr. Then, 6 N hydrochloric acid was used to adjust pH to 6-7, the water bath was cooled to room temperature, centrifuged at 4000 rpm×15 min. The supernatant was added with ethanol to a final concentration of 70% (v/v), placed at 4° C. overnight, centrifuged to obtain the precipitate (crude polysaccharide from *Holothuria scabra*).
Purification:
The obtained crude polysaccharide from *Holothuria scabra* was dissolved in 2 L pure water, centrifuged at 4000 rpm×15 min and the insoluble substances were removed. The supernatant was adjusted with 2N NaOH to pH about 9.5, and H$_2$O$_2$ was added to a final concentration of about 3% (v/v), reacted at 50° C. for 2 hr under stirring and subjected to decolorization. Potassium acetate was added to the decolored reaction solution to a concentration of about 0.5 M, and ethanol was added to a concentration of about 40% (v/v), placed for 4 hr at room temperature, centrifuged at 4000 rpm×15 min. The precipitate was dissolved in 1 L pure water, potassium acetate was added to the obtained solution to a concentration of about 0.5 M, and ethanol was added to a concentration of about 40% (v/v), placed for 4 hr at room temperature, centrifuged at 4000 rpm×15 min. The precipitate was washed with 200 mL of 80% ethanol (v/v) twice, dried under reduced pressure, and about 13.26 g of polysaccharide composition 1 containing Fuc3S4S substituted glycosaminoglycan from *Holothuria scabra* (HSG-1) was got.

About 6.0 g of polysaccharide composition from *Holothuria scabra* (HSG-1) was dissolved in 500 mL of pure water, ultrafiltrated with a 100 kD ultrafiltration package using a Minipole ultrafiltration device. The resulting filtrate was ultrafiltrated with a 30 kD ultrafiltration package with the same device, and the retentate was freeze-dried to obtain about 5.33 g of polysaccharide composition 2 containing Fuc3S4S substituted glycosaminoglycan from *Holothuria scabra* (HSG-2).

Another about 4.0 g of polysaccharide composition 1 (HSG-1) from *Holothuria scabra* was dissolved in 50 mL of pure water, loaded onto a DEAE-cellulose column (diameter 5 cm, bed volume 400 mL), washed with 400 mL of water (flow rate 4 ml/min), eluted with NaCl gradient from 0.5 M to 2 M. The eluted fractions were collected using an automatical collecting instrument at a rate of 10 ml/fraction. Azure solution metachromatic detection method was used to monitor the fractions containing acidic mucopolysaccharides. The fractions containing acidic mucopolysaccharides were combined and dialyzed with a 30 kD dialysis membrane, and freeze-dried to obtain about 3.25 g of polysaccharide composition 3 containing Fuc3S4S substituted glycosaminoglycan from *Holothuria scabra* (HSG-3).
1.3 Detection and Analysis
(1) High Performance Gel Chromatography (HPGPC) Analysis:
Each of the Fuc3S4S substituted glycosaminoglycan-containing polysaccharide compositions from *Holothuria scabra*, i.e., HSG-1, HSG-2 and HSG-3 was prepared into 5 mg/ml sample solution with pure water. The HPGPC analysis conditions were: Agilent 1200 high performance liquid chromatography meter, Shodex SB-804 HQ (8.0 mm ID×300 mm) chromatography column, column temperature 35° C., injection volume 20 μl, mobile phase 0.1 M NaCl solution, flow rate 0.5 ml/min, and measurement by RID detector and DAD detector.

HPGPC analysis spectra of polysaccharide compositions from *Holothuria scabra*, i.e., HSG-1, HSG-2 and HSG-3, are shown in FIG. 1. It can be seen from FIG. 1 that HSG-2 has polysaccharide composition only at the retention time (RT) of about 19 min (mainly FGAG); besides the main peak, HSG-1 also had peaks at the retention time (RT) of about 14 min (mainly FS) and RT of about 22 min (mainly peptide ingredients); except the main peak, the peaks of HSG-3 at RT of about 14 min and RT of about 22 min were lower than that of HSG-1.

(2) Molecular Weight Detection:
Each of HSG-1, HSG-2 and HSG-3 and FGAG reference with series of molecular weights (prepared by the Kunming Institute of Botany, calibrated by HPLC-LALLS) was prepared into sample solution with a concentration of 10 mg/ml using pure water, and HPGPC spectra were measured.

The HPGPC detection conditions were: Agilent 1200 high performance liquid chromatography meter, Shodex SB-804 HQ (8.0 mm ID×300 mm) chromatography column, column temperature 35° C., injection volume 20 μl, mobile phase 0.1M NaCl solution, flow rate 0.5 ml/min, and measurement by RID detector and DAD detector.

HPGPC detection results show that, the polysaccharide composition containing main FGAG peak of HSG-1, HSG-2 and HSG-3 has a weight average molecular weight (Mw) of about 63.2 kD, 63.5 kD and 64.2 kD respectively, and a number average molecular weight (Mn) of about 56.5 kD, 59.7 kD and 58.9 kD respectively; a polydispersity index (PDI) of about 1.12, 1.06 and 1.09, respectively. The result show that FGAG composition (main peak) in the polysaccharides of HSG-1, HSG-2 and HSG-3 exhibit a good uniformity.

(3) Monosaccharide Composition Analysis:

For the detection of HSG-1, HSG-2 and HSG-3, Elson-Morgon method, m-hydroxyldiphenyl method and Cysteine phenol method (Zhang weijie, Biochemical Research Technology of Glycoconjugate 2Ed, Zhejiang University Press, 1999) were used to detect the content of acetyl galactosamine, glucuronic acid and fucose in the polysaccharide composition. The detection results of monosaccharide composition of HSG-1, HSG-2 HSG-3 are shown in Table 1. The results show that, in the three monosaccharide compositions, the molar ratio of hexuronic acid, hexosamine and fucose is in the range of 1: (1±0.3):(1±0.5). In contrast, HSG-1 has higher fucose molar ratio, which is related to the peaks of the more residual FS polysaccharides (RT~14 min), and HSG-2 and HSG-3 have relatively higher content of hexuronic acid and hexosamine, consistent with the effect of further purification.

As shown in FIG. 1, HSG-2 basically do not have peak at Rt~14 min, but its molar content of Fuc is still slightly higher than that of GlcUA and GalNAc, even its molar ratio of Fuc to GlcUA is slightly higher than that of HSG-3, which is in agreement with the find mentioned later that the polysaccharides contain FS, the molecular weight distribution of which is similar to that of FGAG.

TABLE 1

Monosaccharide composition analysis of the Fuc3S4S substituted glycosaminoglycan-containing polysaccharide component from *Holothuria scabra*

|  | Mass percentage (%) | | | Molar ratio |
| --- | --- | --- | --- | --- |
|  | GlcUA | GalNAc | Fuc | GlcUA:GalNAc:Fuc |
| HSG-1 | 15.62 | 18.93 | 16.65 | 1.00:1.05:1.28 |
| HSG-2 | 16.58 | 19.12 | 15.33 | 1.00:0.99:1.11 |
| HSG-3 | 16.64 | 19.82 | 15.06 | 1.00:1.03:1.09 |

Example 2

Preparation of Fuc3S 4S Substituted Oligoglycosaminoglycans-Containing Mixture by Peroxide Depolymerization of Polysaccharide Composition from *Holothuria scabra* (dHSG-1)

2.1 Materials

HSG-2:

polysaccharide composition containing Fuc3S4S substituted glycosaminoglycans prepared by extraction and purification of dried *Holothuria scabra* in Example 1. Mw, ~63.5 kD; PDI, ~1.06.

Reagents:

NaCl, $CH_3COONa$, NaOH, $H_2O_2$, Cu $(CH_3COO)_2$ and other commercially available reagents were analytical grade reagents.

2.2 Preparation 100.3 mg of HSG-2 obtained in Example 1 was placed in a 10 mL reaction tube, dissolved in 3 mL of water, 87.2 mg of NaCl was added to a concentration of 0.5M, 204.1 mg of sodium acetate trihydrate was added to a concentration of 0.5 M, 2.4 mg of copper acetate was added to a concentration of 4.01 nM, and 0.4 mL of 10% $H_2O_2$ was added. The reaction solution was adjusted with 0.1 M NaOH to pH about 7.5, and depolymerized at 35° C. 10 μL sample was taken at intervals of 40 min, and subjected to alcohol precipitation and water dissolution, and detected by HPGPC to confirm the end of the reaction. The reaction was terminated after depolymerization for 3 hr. To the reaction solution 10 mg of disodium ethylenediaminetetraacetate was added, and then 7.5 mL of anhydrous ethanol was added, incubated without shaking and then centrifuged at 3000 rpm for 15 min. The precipitate was dissolved in 3 mL of water, and purified by $OH^-$ type DEAE anion exchange resin column combined with $H^+$ type cation exchange resin column, the fractions containing acidic mucopolysaccharides were collected, and adjusted with 0.1M NaOH solution to neutral pH, dialyzed with 1 kD dialysis bag for 48 hr. The dialysis retentate was freeze-dried, 75 mg of Fuc3S4S substituted oligglycosaminolycan product 1 (dHSG-1) was got.

2.3 Detection

Methods:

Molecular weight and distribution were measured by HPGPC. The content of acetylgalactosamine (D-GalNAc) was measured by Elson-Morgon method. The content of glucuronic acid (D-GlcUA) was measured by carbazole method. D-GalNAc/L-Fuc molar ratio was calculated by $^1H$ NMR methyl peak integral area. NMR spectra were got by AVANCE AV 500 superconducting nuclear magnetic resonance meter (500 MHz) (Bruker company, Switzerland).

Results:

The analysis results of physicochemical properties and monosaccharide compositions of HSG-2 and its peroxide depolymization product dHSG-1 are shown in table 1. Compared with dHSG-2, the Mw of dHSG-1 was significantly reduced by more than 7 fold. The monosaccharide composition analysis shows that, the composition ratio of hexosamine and hexuronic acid in HSG2 and dHSG-1 is basically stable, the ratio of deoxyhexose (Fuc) has been decreased, relate to the decrease of FS impurities.

TABLE 2

Analysis results of physicochemical properties and monosaccharide compositions of HSG-2 and dHSG-1 from *Holothuria scabra*

| Sample | Molecular weight (Mw, kD) | PDI | monosaccharide composition (molar ratio) GlcUA:GalNAc:Fuc |
| --- | --- | --- | --- |
| HSG-2 | 63.5 | 1.06 | 1.00:0.99:1.11 |
| dHSG-1 | 8.83 | 1.30 | 1.00:1.02:1.03 |

Some spectra of NMR spectroscopy of dHSG-1 are shown in FIG. 2-3. $^1H$ NMR spectrum in FIG. 2A shows that between 5.0-5.7 ppm, there is a signal peak of α-L-Fuc terminal at 5.32 ppm. Based on the correlation signals in $^1H$-$^1H$ COSY, it can be seen that the proton signals at C2, C3, C4-positions are located at about 3.96, 4.53, 4.96 ppm, respectively. In further showed the C6-methyl signal is located at about 1.2-1.4 ppm, and the C5-proton signal is located at about 4.88 ppm. Compared with the corresponding proton signals of unsubstituted Fuc, the proton signals are shifted to downfield by more than 0.6 ppm, based on which it is concluded that sulfate substitution is present at C3, C4-positions. Obviously, Fuc contained in dHSG-1 is mainly α-L-Fuc3S4S. It is concluded by combination of FIGS. 2 and 3 that, dHSG-1 contains a small amount of α-L-Fuc4S and –2S4S. According to the integral proportion of α-L-Fuc terminal hydrogen shown in $^1$H NMR spectrum, it is concluded that in the fucose branches contained in dHSG-1, the proportion of Fuc3S4S, Fuc4S, Fuc2S4S are about 82%, 12% and 6% respectively.

The $^{13}$C NMR spectrum (FIG. 2B) shows that, terminal hydrogen signal of α-L-Fuc3S4S is located at about 102 ppm, methyl signal is located at about 18.6 ppm, other C signals on its sugar ring can be clearly assigned by $^1$H-$^{13}$C HSQC correlation signals. Wherein compared with C signal at the corresponding position of unsubstituted Fuc, there are significant downfield shifts of C signal peaks at C3 and C4, indicating the presence of sulfate substitution at these positions.

The terminal C signal of 13-D-GlcUA is located at about 105.6 ppm (FIG. 2B), HSQC spectrum shows that the terminal hydrogen signal is located at about 4.48 ppm, $^1$H-$^1$H COSY spectrum shows the proton signals at C2-C5 positions are located at about 3.62, 3.66, 3.94 and 3.70 ppm. Compared with the proton signal at the corresponding position of unsubstituted α-D-GlcUA, proton signals at C3 and C2-positions are shifted downfield by about 0.3-0.5 ppm. It can be seen from the $^1$H-$^1$H ROESY signals (FIG. 3) that, α-L-Fuc3S4S contained in HSG is linked to β-D-GlcUA by α1-3 glycosidic linkage.

C6 signal on β-D-GlcUA is overlapped with the C7 signal on the β-D-GalNAc, the other $^{13}$C signals on sugar ring are assigned by $^1$H-$^{13}$C HSQC spectrum. C3 signal is located at about 82 ppm, which is shifted downfield by 3-4 ppm compared with the unsubstituted C3 signal, further demonstrating that there are substituted fucose branches at this position.

By combination of the terminal $^{13}$C signal (at about 102 ppm, FIG. 2B) of β-D-GalNAc and $^1$H-$^{13}$C HSQC spectrum, it is concluded that the terminal proton signal is located at about 4.58 ppm. Based on the $^1$H-$^1$H COSY spectrum, it is concluded that C2-C5 proton signals are located at about 4.05, 3.92, 4.79 and 4.01 ppm, respectively, and C6 proton signal is located at about 4.23 and 4.31 ppm. Compared with the corresponding proton signals of unsubstituted β-D-GalNAc, proton signals at C4, C6-positions are shifted downfield by about 0.5-0.7 ppm, thus it is concluded that the hexosamine contained in dHSG-1 is mainly β-D-GalNAc4S6S. The characteristic methyl proton signal of acetyl on β-D-GalNAc is located at about 2.04 ppm.

TABLE 3

$^1$H/$^{13}$CNMR signal assignments of dHSG-1

| | H-1 | H-2 | H-3 | H-4 | H-5 | H-6 | H-8 |
|---|---|---|---|---|---|---|---|
| β-GalNAc-4S6S | 4.58 | 4.05 | 3.92 | 4.79 | 4.01 | 4.23/4.31 | 2.05 |
| β-GlcUA | 4.48 | 3.62 | 3.66 | 3.94 | 3.70 | — | — |
| α-Fuc-3S4S | 5.32 | 3.96 | 4.53 | 4.96 | 4.88 | 1.36 | — |

| | C-1 | C-2 | C-3 | C-4 | C-5 | C-6 | C-7 | C-8 |
|---|---|---|---|---|---|---|---|---|
| β-GalNAc-4S6S | 102.6 | 54.0 | 78.1 | 79.2 | 74.3 | 69.6 | 25.1 | 177.5 |
| β-GlcUA | 105.8 | 75.9 | 81.8 | 78.0 | 79.0 | 177.5 | — | — |
| α-Fuc-3S4S | 102.4 | 69.0 | 78.1 | 82.0 | 69.0 | 18.6 | — | — |

Based on the $^{13}$C NMR and DEPT135 spectra, methylene peaks at C6 position is located at about 69.6 ppm, which is shifted downfield by about 6 ppm compared with the C6 peak of unsubstituted β-D-GlcUA, further demonstrating that sulfate substitution is present at C6. The characteristic signals of C2 and C8 on β-D-GalNAc are located at about 54 ppm and about 25 ppm, which is consistent with the structure feature of acetylgalactosamine. The $^{13}$C signals at C3-C5 can be assigned by $^1$H-$^{13}$C HSQC spectrum as shown in FIG. 3, and its C7 signal is overlapped with the C6 signal of β-D-GlcUA.

To summarize the chemical structure analysis, dHSG-1 is a kind of glycosaminoglycan derivative having α-L-Fuc3S4S as main branch substitution (about 82%), with the basic structural unit is as follows:

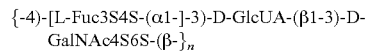

{-4)-[L-Fuc3S4S-(α1-]-3)-D-GlcUA-(β1-3)-D-GalNAc4S6S-(β-}$_n$

According to the above chemical structure analysis, it can be known that, with respect to the reported FGAG compositions, dHSG-1 has the characteristics as follows: (1) fucose branches are mainly α-L-Fuc3S4S, and (2) there is 4,6-disulfated on GalNAc backbone. Compared with FGAG from *Stichopus japonicas, Thelenota ananas* and Brazilian sea cucumber, the branch substitution type of dHSG-1 is simple (mainly α-L-Fuc3S4S), the C6 of backbone hexosamine is completely substituted by sulfated group (mainly β-D-GalNAc4S6S), and therefore its chemical structure has better uniformity.

Example 3

Preparation of Fuc3S4S Substituted Oligoglycosaminoglycan Mixture by Deacylated Deaminated Depolymerization of the Polysaccharide Composition from *Holothuria scabra* (dHSG-2)

3.1 Materials

HSG-3:

polysaccharide composition containing Fuc3S4S substituted glycosaminoglycan obtained by extraction and purification of dried *Holothuria scabra*. Mw, ~64.2 kD; PDI, ~1.09.

Reagents:

hydrazine hydrate, hydrazine sulfate, anhydrous ethanol, sodium borohydride and other reagents were commercially available analytical reagents.

3.2 Preparation (1) Preparation of Partial Deacetylated Product:

360 mg of the polysaccharide composition HSG containing Fuc3S4S substituted glycosaminoglycan from *Holothuria scabra* in Example 1 was put in a reaction tube, added 14.5 mg of hydrazine sulfate as catalyst, and then added 1.45 mL of hydrazine hydrate, under the protection of nitrogen, stirred at 250 rpm, reacted at 70° C. for 12 hr. After the reaction completed, the reaction solution was added with ethanol to a concentration of ethanol of 80% (v/v), and centrifuged at 3000 rpm for 15 min. The precipitate was washed with 5 ml 80% (v/v) ethanol aqueous solution, dissolved in deionized water and dialyzed with a 3.5 kD dialysis bag in pure water for 3 days. Dialyzed retentate was freeze-dried to obtain 53.0 mg of partial deacetylated product of HSG-3. $^1$H NMR detection showed that the deacetylation degree of the obtained product was about 12%.

(2) Preparation of Deaminated Depolymerization Product dHSG-2:

40 mg of partial deacetylated product of HSG-3 of step 1 was accurately weighed and put into a reaction flask, and dissolved in 2 mL of water. Under the ice bath condition, 4 mL 5.5 M nitrous acid solution (pH 4) was added, depolymerized under ice bath for 10 min, and then 0.5 M NaOH solution was added to adjust pH to 9-10 to terminate the reaction.

(3) Terminal Reduction and Product Purification:

The reaction solution of step (2) was added with 2 mL of 0.1 mol/L sodium hydroxide solution containing 0.5 mol/L of sodium borohydride, heated at 50° C. for 40 min to reduce the aldehyde groups of nitrous acid depolymerization products. After the reaction completed, the reaction solution was cooled to room temperature, and 0.5 M $H_2SO_4$ was added dropwise to remove excessive sodium borohydride, and finally neutralized with 0.5 M NaOH, dialyzed with a 1.0 kDa dialysis bag in pure water for 24 hr. The resulting dialysis retentate was subjected to G50 column chromatography and with formetachromasia detection. The eluted fractions containing acidic mucopolysaccharide were collected and combined, and the resulting eluted solution was freeze-dried, about 38.5 mg of deaminated depolymerization product dHSG-2 was got.

3.3 Detection

The detection method was the same as in Example 2. HPGPC monitoring results show that, after deacylated deaminated depolymerization, the resulting product still contains small amounts of polysaccharides with a Mw of about 60 kD (including FS and neutral glucan), the high molecular weight composition can be easily removed by G50 gel chromatography. The HSG-3 deaminated depolymerization product dHSG-2, which was purified by G50 gel chromatography, has a Mw of about 7.83 kD, and a polydispersity index (PDI) of about 1.38.

The monosaccharide composition of dHSG-2 includes GlcUA, GalNAc and Fuc. The ratio of the three monosaccharide compositions was about 1.00:0.89:1.02. In dHSG-2 product the GalNAc content was slightly less than that of dHSG-1, which was basically in agreement with the integral area ratio of methyl signal peak of acetyl on GalNAc at about 2.02 ppm to methyl signal peak of Fuc at about 1.23-1.36 ppm showed in $^1$H NMR spectrum, and was also basically in agreement with the deacetylation degree of partial deacetylation process.

The $^1$H, $^{13}$C NMR and 2D correlation spectra show that, the main $^1$H, $^{13}$C signal peaks of dHSG-2 and the main correlation peaks in its 2D correlation spectrum are the same or similar to that of dHSG-1. However, dHSG-2 exhibits carbon, hydrogen signals assigned to 2,5 dehydrated talose (AnTol) different from those of dHSG-1.

Based on the spin coupling system shown in $^1$H-$^1$H COSY spectrum, hydrogen in AnTol saccharide ring can be easily assigned, the two H signals at C1 are located at about 3.68 (H1) and 3.80 ppm (H1'), the H signals at C2 to C5 are located at about 4.13 (H2), 4.54 (H3), 5.04 (H4) and 4.51 ppm (H5), respectively, and the two H signals at C6 are located at about 4.35 (H6) and 4.18 ppm (H6') respectively. Based on the heteronuclear correlation signals shown in $^1$H-$^{13}$C HSQC spectrum, the carbon signals of AnTol can be easily assigned, the signals of C1 to C6 are located at about 63.8, 83.9, 78.9, 80.4, 80.3 and about 71.0 ppm, respectively.

Compared with the hydrogen and carbon signals at corresponding positions of unsubstituted AnTol, C4 and C6 signals of terminal AnTol of dHSG-2 are significantly shifted downfield, therefore, it is concluded that there is 4,6-disulfated substitution, i.e., the terminal AnTol group is AnTol4S6S. This is consistent with the structure of β-D-GalNAc4S6S on backbone of dHSG-1, meanwhile it indicates that the sulfate groups are basically not affected during the deacylated deamination reaction.

According to the integral proportion of terminal hydrogen of α-L-Fuc in $^1$H NMR spectrum, it is concluded that the fucose branches contained in dHSG-2 also includes Fuc3S4S, Fuc4S, Fuc2S4S, in which the proportion of Fuc3S4S is about 83%.

In addition, it is demonstrated by the NMR spectrum of deacylated deaminated depolymerization product containing non-reduced terminal (2,5-dehydrated talose, AnTal) prepared in parallel by the present invention, that the C1 carbonyl of the terminal AnTal is easily bond to a molecule of water to form a -diol hydrate structure.

Example 4

Preparation of Fuc3S4S Substituted Oligoglycosaminoglycan Mixture (dHSG-3) by β-Eliminative Depolymerization of Polysaccharide Composition from *Holothuria scabra*

4.1 Materials

HSG-1:

polysaccharide compositions containing Fuc3S4S substituted glycosaminoglycan which was extracted and purified from dried *Holothuria scabra* in Example 1. Mw, ~63.2 kD; PDI, 1.09

Reagents:

benzethonium chloride, benzyl chloride, anhydrous ethanol, sulfuric acid, sodium hydroxide, metallic sodium and other reagents were commercially available analytical reagents.

4.2 Preparation (1) Preparation of quaternary ammonium salt of HSG 200.4 mg of HSG-1 was dissolved in 8 mL of deionized water. 500 mg of benzethonium chloride was dissolved in another 8 mL of deionized water. The benzethonium chloride solution was added dropwise into the HSG solution under the conditions of continuous shaking. White precipitate appeared in the solution. The solution was centrifuged at 4000 rpm for 20 min to obtain the precipitate, which was washed with 100 mL water for three times under shaking. The precipitate was dried in a vacuum oven under reduced pressure at room temperature for 24 hr and 490 mg of quaternary ammonium salt of HSG-1 was obtained.

(2) Preparation of Partial Benzyl-Esterified Product of Carboxyl of Quaternary Ammonium Salt of HSG-1

490 mg of quaternary ammonium salt of HSG-1 obtained in step 1 was put in a 50 mL round bottom flask, 13.2 mL of dimethylformamide (DMF) was added. After the sample was dissolved, 6.6 mL of benzyl chloride was added and reacted at 35° C. in a closed atmosphere for 2 hr with stirring at 500 rpm/min. After the reaction completed, 20 mL saturated NaCl and 160 mL anhydrous ethanol were added. The reaction solution was centrifuged at 4000 rpm for 15 min, and the precipitate was washed with 80% ethanol saturated with sodium chloride for three times. The resulting precipitate was dissolved in 10 mL of deionized water, and dialyzed using a dialysis bag with the molecular weight cutoff of 3.5 kD (dialyzed against running water for 12 hr, and against deionized water for 36 hr). Dialysis retentate was concentrated under reduced pressure to 5 mL, and a small amount of which was freeze-dried for $^1$HNMR spectrum analysis. The results of $^1$HNMR spectrum showed that the degree of carboxyl esterification was 26.9%. The rest of concentrated dialysis solution was subjected to cation exchange resin (H$^+$ type, column bed 45 cm×5 cm) to convert into its hydrogen type, and the eluted fractions containing acidic mucopolysaccharide were collected.

Under the monitor of conductivity meter, the eluted fractions were titrated with 0.4 M tetrabutyl ammonium hydroxide to pH 8, and then the resulting solution was freeze dried, 245.5 mg of TBA type quaternary ammonium salt of partial benzyl-esterified product of HSG-1 was got.

(3) β-Eliminative Depolymerization 245.5 mg of TBA type quaternary ammonium salt of benzyl-esterified product of carboxyl obtained in step 2 was put into a 50 mL round-bottomed flask, added 4.9 mL DMF and freshly prepared 4.9 mL 0.04M EtONa/EtOH. Under 25° C. and nitrogen protection, reacted for 4 hr with stirring at 500 r/min. After the reaction completed, the reaction solution was sequentially added with 9.8 mL saturated NaCl solution and anhydrous ethanol to 100 mL, and then centrifuged at 4000 rpm for 15 min. The resultant precipitate was β-eliminative depolymerization product of partial benzyl-esterified HSG-1(dHSG-3-0).

4) Debenzylation 10 mL 0.1 M NaOH was added into the precipitate dHSG-3-0 obtained in step 3 to dissolve it completely. After alkaline hydrolysis at 35° C. for 1 hr, 1 M HCl solution was added to adjusted pH to neutral. Anhydrous ethanol was added to a concentration of about 80% (v/v), and centrifuged at 4000 rpm for 15 min. The precipitate was dissolved in pure water, ultrafiltrated using a ultrafiltration tube having molecular weight cutoff of 30 kDa (study showed that such ultrafiltration step may effectively remove polysaccharide compositions that cannot be removed by β-eliminative depolymerization, including fucan FS and neutral polysaccharide NP, which have molecular weight distribution close to or overlapped prototype FGAG from *Holothuria scabra*). The resulting filtrate with a molecular weight of less than 30 kDa was transferred into a 1 kD dialysis bag, and dialyzed against deionized water for 36 hr. The resulting dialysis retentate was freeze-dried, about 114 mg of Fuc3S4S substituted oligolycosaminoglycan mixture product (dHSG-3) was got.

4.3 Detection

Detection of physicochemical properties and spectral analysis of dHSG-3 were the same as in Example 2.

Analysis results of physicochemical properties and monosaccharide compositions of HSG-1 and its depolymerization product dHSG-3 are shown in Table 4. The detection results show that compared with HSG-1, the molecular weight of dHSG-3 is significantly decreased. The analysis results of monosaccharide composition show that compared with HSG-1, based on the molar ratio to GlcUA the proportion of GalNAc is increased, whereas the proportion of Fuc is decreased, the former is related to the β-eliminative reaction of partial GlcUA, the latter is related to further removal of FS impurity in polysaccharide composition of HSG-1, and the molar ratio of monosaccharide composition GalNAc to Fuc contained in dHSG-3 is in agreement with the integral ratio of methyl signal peaks contained in such two glycosyl shown in $^1$H NMR.

TABLE 4

Detection results of physicochemical properties and monosaccharide compositions of HSG-1 and dHSG-3 from *Holothuria scabra*

| Sample | Molecular weight (Mw, kD) | PDI | Optical rotation ($[\alpha]_D^{20}$) | Monosaccharide composition (molar ratio) GlcUA:GalNAc:Fuc |
|---|---|---|---|---|
| HSG-1 | 63.2 | 1.26 | −68.5° | 1.00:1.05:1.28 |
| dHSG-3 | 8.63 | 1.41 | −54.6° | 1.00:1.13:1.12 |

A UV spectrophotometer was used to scan the sample with a wavelength range of 190 nm-400 nm. dHSG-3 has the maximum UV absorption at 232 nm, which is consistent with the presence of unsaturated bond ΔUA.

NMR spectrum results show that, compared with the spectrum of compound dHSG-1, the $^1$H NMR spectrum of dHSG-3 has new signal peaks at about 5.76 and 5.82 ppm, according to the $^1$H NMR correlation spectrum, these signals can be assigned to the characteristic signal of 4H on 4-deoxy-threo-hex-4-enopyranosyluronic acid-1-yl (ΔUA), which is the β-eliminative product of β-D-GlcUA (Table 5, FIG. 4).

The $^1$H-$^1$HCOSY spectrum and TOCSY spectrum of dHSG-3 clearly show that the signals of H4, H3, H2 and H1 of ΔUA are coupling associated (FIG. 5). The ROESY spectrum shows that, L-Fuc branch is linked to β-D-GlcUA or ΔUA by α(1-3) glycosidic linkage (FIG. 5). Compared with the terminal H signal of L-Fuc linked to β-D-GlcUA, the terminal H signal of Fuc linked to ΔUA is obviously present at lower field (FIG. 4).

In the $^{13}$C-NMR spectrum, C1 peaks of β-D-GlcUA and β-D-GalNAc are present at about 97-104 ppm, while C1 peak of ΔUA is present at about 103.5 ppm, and the chemical shift of C4 is at 106.8 ppm, the chemical shift of C5 is at about 148.5 ppm (FIG. 4).

TABLE 5

$^1$H/$^{13}$C NMR signal assignment of compound dHSG-3 (δ [ppm])

| | H-1 | H-2 | H-3 | H-4 | H-5 | H-6 | H-8 |
|---|---|---|---|---|---|---|---|
| β-GalNAc4S6S | 4.56 | 4.05 | 3.99 | 4.75 | 4.03 | 4.25, 4.33 | 2.04 |
| | 4.59 | 4.11 | 4.16 | 4.98 | 4.08 | 4.27, 4.37 | 2.09 |
| ΔUA | 4.49 | 3.62 | 3.67 | 4.01 | 3.70 | | |
| β-GlcUA | 4.91 | 3.88 | 4.66 | 5.74 | | | |
| α-Fuc3S4S | 5.32 | 3.95 | 4.53 | 4.97 | 4.82 | 1.38 | |
| | 5.25 | 3.96 | 4.59 | 4.88 | 4.32 | 1.28 | |

| | C-1 | C-2 | C-3 | C-4 | C-5 | C-6 | C-7 | C-8 |
|---|---|---|---|---|---|---|---|---|
| β-GalNAc4S6S | 102.2 | 54.3 | 78.1 | 78.8 | 74.3 | 69.6 | 25.1 | 177.5 |
| | 102.2 | 54.1 | 78.1 | 78.8 | 74.3 | 69.6 | 25.1 | 177.5 |
| ΔUA | 105.8 | 75.8 | 81.5 | 78.0 | 79.6 | 169.0 | | |
| β-GlcUA | 103.5 | 72.6 | 80.3 | 109.2 | — | 177.5 | | |
| α-Fuc3S4S | 101.9 | 68.0 | 78.0 | 81.8 | 68.0 | 18.6 | | |
| | 100.5 | 68.0 | 78.0 | 81.8 | 68.0 | 18.6 | | |

Taking the hydrogen spectrum, carbon spectrum and correlation spectra into consideration, in the main chain monosaccharide compositions of dHSG-3, D-GlcUA and D-GalNAc are linked to each other by β(1→3) and β(1→4) glycoside linkages to constitute a polysaccharide backbone, and thus form a disaccharide structure unit. According to the chemical shifts of H2, H3 of GlcUA combined with $^1$H-$^1$H ROESY and $^1$H-$^{13}$C HMBC, it is concluded that L-Fuc is linked to β-D-GlcUA by α(1→3) glycosidic linkage, and the main L-Fuc branch type is Fuc3S4S. Obviously, in dHSG-3, non-reducing terminal hexuronic acid is mainly ΔUA.

It is concluded based on the α-L-Fuc terminal hydrogen integral ratio of α-L-Fuc shown in the $^1$H NMR spectrum, fucose branch contained in dHSG-3 includes the structure types, such as α-L-Fuc3S4S, α-L-Fuc4S, α-L-Fuc2S4S, and the main type is α-L-Fuc3S4S. Based on molar ratio, α-L-Fuc3S4S accounts for about 82% of the total fucosyl residues.

Example 5

Carboxyl Reduction and Reductive Amination of Reducing Terminal Carbonyl of Fuc3S4S Substituted Oligoglycosaminogly Mixture (dHSG-3)

5.1 Materials
dHSG-3:
Fuc3S4S substituted oligoglycosaminogly mixture obtained in Example 4.
Reagents:
1-ethyl-3-(3-dimethylaminopropyl)carbodiimide (EDC), 1-phenyl-3-methyl-5-pyrazolone (PMP), tyramine hydrochloride, sodium cyanoborohydride, sodium borohydride, HCl, NaCl and other reagents were commercially available analytical reagents.

5.2 Preparation (1) Preparation of Carboxyl Reductive Derivative:
30 mg dHSG-3 was dissolved in 5 ml water, and adjusted to pH 4.75 with 0.1 N HCl. 90 mg EDC was added within 5 mins, and adjusted with 0.1 N HCl to maintain pH at 4.75. 360 mg $NaBH_4$ was added slowly with stirring, and the reaction solution was put in water bath at 50° C. for 2 hr. A small amount of acetic acid was added dropwise to remove the excessive $NaBH_4$, and then dialyzed against deionized water with a 3.5 KD dialysis bag. The dialysis retentate was freeze-dried about 24.6 mg of carboxyl reductive Fuc3S4S substituted oligoglycosaminogly mixture was got (Yield 78.3%).

(2) Preparation of Terminal Reductive Aminated Derivative (2):
30 mg dHSG-3 was dissolved in 2.5 ml 0.2 mM phosphate buffer (PBS, pH 8.0) and with stirring sequentially added 24 mg tyramine hydrochloride and 9 mg sodium cyanoborohydride, incubated in water bath at 35° C. for 5 d, added 7.5 ml of 95% ethanol, centrifuged at 3000 rpm for 15 min. The precipitate was washed with 3 ml 95% ethanol twice, evaporated under reduced pressure to remove ethanol. The washed precipitate was dissolved in 2 ml of 0.1% NaCl, centrifuged at 3000 rpm for 15 min to remove insoluble matters. The supernatant was transferred into a 3.5 kD dialysis bag, dialyzed against deionized water (100 ml×3) for 36 hr, and the dialysis retentate was freeze-dried, about 20.5 mg terminal reductive aminated Fuc3S4S substituted oligoglycosaminogly mixture was got (Yield 68%).

5.3 Detection (1) dHSG-3a Detection:
IR spectroscopy of dHSG-3a was measured using a liquid pool detection method according to the reference (*Carbohydr. Res*, 1978, 63: 13-27); The molar ratio of $-OSO_3^-/-COO^-$ was determined by conductance titration method (Weijie Zhang, Biochemical Research Technology of Glycoconjugate 2Ed, Zhejiang University Press, 1999, 409-410). The results show that there is no signal of carboxyl of β-D-GlcUA in the liquid pool IR spectrum of dHSG-3a, suggesting that β-D-GlcUA has been reduced into β-D-Glc; the results of conductivity detection show that there is only one inflection point in the conductivity titration curve, the inflection point is from the sulfate group. No inflection point on the curve of conductivity change due to carboxyl group indicates that dHSG-3 in the β-D-GlcUA has been reduced.

(2) dHSG-3b Detection:
Monosaccharide composition and NMR spectrum of dHSG-3b were analyzed according to the method as the same in Example 1. The results show that in the monosaccharide composition of dHSG-3b, the molar ratio of D-GalNAc:D-GlcUA:L-Fuc is about 1.00:1.02:1.11, which is basically in agreement with the theoretical calculation result of structural unit of dHSG-3b: $^1$HNMR ($D_2O$, δ [ppm]): 7.25 (2', 6'H); 6.91 (3', 5'H); 5.74 (ΔUA, 4H), 5.32, 5.25 (L-Fucα1H); 3.38 (8'H); 2.82 (7'H); 2.02 (D-GalNAc, CH3); 1.26-1.36 (L-Fuc, $CH_3$). Integral ratio of methyl hydrogen to benzene hydrogen of L-Fuc is about 11, indicating that the reducing terminal of the resulting product is all reductively tyraminated.

Example 6

Comparison of Anticoagulant Activities of Native FGAG and Depolymerization Product with Different Sulfation Patterns of Fuc Branches 6.1 Materials (1) FGAGs:
AJG, TAG, IBG, LGG, HSG and PGG, prepared by extraction of commercially available dried *Apostichopus japonicus, Thelenota ananas, Isostichopus badionotus, Ludwigothurea grisea, Holothuria scabra* and *Pearsonothuria graeffei*, based on the preparation method of HSG-2 in Example 1.

(2) dFGAGs:
dAJG, dTAG, dIBG, dLGG, dHSG and dPGG, prepared by peroxide depolymerization and purification using AJG, TAG, IBG, LGG, HSG and PGG as starting materials, similar to the preparation method of dHSG-1 in Example 2.

(3) Reagents and Instruments:
Human quality control plasma, activated partial thromboplastin time (APTT) kit, prothrombin time (PT) kit were from Teco Medical (Germany); low molecular weight heparin (LMWH), enoxaparin sodium were from Sanafi Aventis company (France); prekallikrein (PK), kallikrein substrate, thrombin (IIa) 100 NIHU/mg, thrombin chromogenic substrate (CS-0138) 25 mg/vial, heparin cofactor II (HC-II) 100 g/vial, f.VIII detection kit were from HYPHEN BioMed company (France); factor VIII (f.VIII) 200 IU/single were from Shanghai RAAS blood products company; dermatan sulfate (DS) was from Sigma company (United States), oversulfated hondrointin sulfate (OSCS) was from Serva Electro-phoresis GmbH company (Germany); microplate reader was from Bio Tek Inc. (US); Chronolog-700 platelet aggregation meter (US).

6.2 Methods (1) Detection of Anticoagulant Activity:
The FGAGs, dFGAGs and reference samples were prepared into a series of concentrations using saline solution. Quality control plasma, detection kit and MC-4000 coagulation analyzer were used to detect the effect of the sample solutions on APTT and PT of human quality control plasma according to the instructions of the kits.

(2) Detection of Inhibition Activity on Endogenous Factor X Enzyme (f.Xase):
30 μL of each of series concentration of FGAG and dFGAG solutions and 30 μL of f.VIII (2 IU/mL) were mixed, and according to the method of the instruction of the f.VIII detection kit, f. IXa reagent, f.Xa reagent and f.Xa substrate (SXa-11) were sequentially added. $OD_{405\ nm}$ was measured. $EC_{50}$ values of f.Xase inhibition by each sample were calculated according to the method of reference (Blood, 2006, 107:3876-3882).

(3) Test of HCII-Dependent Antithrombin (f.IIa) Activity:
The sample solutions at a series of concentrations were added into 96-well plates, respectively, and then sequentially added 30 μL HC-II (1 μM), f.IIa (10 U/mL) and CS-0138

(4.5 mM, chromogenic substrate), incubated at 37° C. for 2 min. $OD_{405\ nm}$ was measured and $EC_{50}$ values of IIa inhibition by each sample were calculated.

(4) Detection of F.XII Activation:

30 μL sample and reference solution at a series of concentrations were added into 96-well plates, respectively, and then sequentially added 30 μL f.XII (25 g/mL), 30 μL PK (620 nM) and 30 μL chromogenic substrate, incubated at 37° C. for 1 min. OD405 nm was measured.

(5) Detection of Platelet Activation Activity:

Anticoagulant platelet-rich plasma (PRP) and platelet poor plasma (PPP) were collected from healthy volunteers.

Among the several FGAGs, the HCII-dependent anti-f.IIa activities are within the range of about 300-400 ng/ml. After depolymerization, the activities of the dFGAGs are all stronger than that of the native forms, $IC_{50}$ values are within the range of about 130-250 ng/ml. In relative terms, HSG and dHSG have the strongest activities, whereas IBG and dIBG have the weakest activities.

Obviously, PGG/dPGG has the L-Fuc sulfation features similar to HSG/dHSG. Correspondingly, the potency of its anticoagulant activity and the activity of coagulation factor activity inhibition are also basically the same.

TABLE 6

Anticoagulant activities of FGAGs and their depolymerization product dFGAGs

| | Molecular weight (kD) | Sulfation pattern of Fuc branch (%) (%)[a] | | | | | $-SO_4^-/$ $COO^{-a}$ | $2 \times APTT^b$ (μg/ml) | Xase[c] (ng/ml) | IIa/HCII[c] (ng/ml) |
| | | -2S4S | -3S | -4S | -3S4S | -0S | | | | |
|---|---|---|---|---|---|---|---|---|---|---|
| AJG | 63 | 60 | / | 10 | 30 | / | ~3.9 | 2.20 | 12.2 | 375 |
| dAJG | 12.5 | | | | | | | 5.64 | 16.8 | 206 |
| TAG | 66 | 59 | 9 | 14 | 18 | / | ~3.6 | 2.49 | 14.2 | 409 |
| dTAG | 11.6 | | | | | | | 5.78 | 10.6 | 144 |
| IBG | 65 | 92 | / | 4 | 4 | / | ~4.0 | 2.50 | 14.4 | 497 |
| dIBG | 13.8 | | | | | | | 3.48 | 9.9 | 248 |
| LGG | 60 | 10 | 30 | 22 | 21 | 17 | ~2.5 | 3.36 | 18.6 | 381 |
| dLGG | 10.3 | | | | | | | 8.35 | 22.2 | 253 |
| HSG | 62 | 5 | / | 10 | 85 | / | ~3.9 | 2.97 | 19.4 | 297 |
| dHSG | 10.2 | | | | | | | 3.73 | 12.4 | 132 |
| PGG | 60 | 2 | / | 16 | 82 | / | ~3.8 | 2.86 | 18.2 | 302 |
| dPGG | 12.2 | | | | | | | 3.80 | 11.8 | 137 |
| LMWH | 4.5~5.5 | / | | | | | >1.8 | 7.80 | 68.8 | 184 |
| DS | 42 | / | | | | | ~1.4 | 65.1 | 2549 | 67 |

[a]Mole percentage or molar ratio;
[b]drug concentration required for doubling APTT;
[c]based on $EC_{50}$;

The platelet aggregation-inducing activity of the FGAG, dFGAG sample solutions at a series of concentrations was measured by turbidimetry using Chronolog-700 platelet aggregation meter, wherein the FGAG, dFGAG sample solutions were prepared by dissolving FGAG, dFGAG in saline solution.

6.3 Results (1) Anticoagulant Activity:

The anticoagulant activities of FGAGs, dFGAGs and reference are shown in Table 6.

Different sulfation patterns and their composition ratios of fucose branches of FGAGs and dFGAGs from different species were calculated according to the integral of $^1H$ NMR spectra of dFGAGs (FIG. 6). It can be seen from the data shown in Table 6 that, the concentration for doubling APTT of human quality control plasma of native FGAGs is at about 2.2-3.3 g/ml. The difference among the effect on APTT activity between different FGAGs is not significant; the difference among the activities of dFGAGs after depolymerization is increased, wherein the dIBG containing Fuc2S4S as main branches has the strongest activity, and dHSG is close to it, dLGG has the weakest activity.

Some FGAGs have $IC_{50}$ values of f.Xase inhibition of between about 12.2-19.4 ng/ml, and the difference among their activity potency is not significant. After depolymerization, except that the activities of dAJG and dLGG are weaker than that of the native forms, the activities of other dFGAGs are stronger than that of the native forms, whereas the differences of the potency of f.Xase inhibition activities among dFGAGs are increased, wherein dIBG has the strongest activity, and dHSG had relatively strong activity, dLGG has the weakest activity.

(2) Detection of f.XII Activation Activity:

The activation activity of FGAGs from different species and their depolymerization product dFGAGs on f.XII are shown in FIG. 7. Compared with other FGAGs, the f.XII activation activities of HSG and PGG with Fuc3S4S as main fucose branch are significantly weak, and their corresponding depolymerization products also have the similar feature. In contrast, the content of sulfate groups on the backbone and branches of HSG are higher than that of LGG, but slightly higher than that of TAG, close to that of AJG, and slightly lower than that of IBG, whereas their f.XII activation activities are all significantly lower, indicating that f.XII activation of FGAG compositions is not just dependent on the loading capacity of its negative charge, but is related to sulfation patterns of the branch.

(3) Detection of Platelet Activation Activity:

Effect of FGAGs and dFGAGs on platelet activity is shown in Table 7.

TABLE 7

Effect of FGAGs and their depolymerization product dFGAGs on platelet aggregation in healthy volunteers (n = 3)

| Sample | | Aggregation rate (%) | Sample | | Aggregation rate (%) |
|---|---|---|---|---|---|
| Con. | — | 9 ± 4 | ADP | 10 μM | 93 ± 7 |
| AJG | 30 μg/ml | 62 ± 15 | dAJG | 60 μg/ml | 27 ± 11 |
| TAG | 30 μg/ml | 28 ± 6 | dTAG | 60 μg/ml | 14 ± 3 |
| IBG | 30 μg/ml | 65 ± 20 | dIBG | 60 μg/ml | 76 ± 14 |
| LGG | 30 μg/ml | 27 ± 11 | dLGG | 60 μg/ml | 35 ± 8 |

TABLE 7-continued

Effect of FGAGs and their depolymerization product dFGAGs on platelet aggregation in healthy volunteers (n = 3)

| Sample | | Aggregation rate (%) | Sample | | Aggregation rate (%) |
|---|---|---|---|---|---|
| HSG | 30 μg/ml | 13 ± 6 | dHSG | 60 μg/ml | 9 ± 3 |
| PGG | 30 μg/ml | 14 ± 5 | dPGG | 60 μg/ml | 8 ± 3 |

It can be seen from the results shown in Table 7, HSG and PGG with Fuc3S4S as main fucose branch also have significantly weaker platelet activation activity in healthy volunteers, and their corresponding depolymerization products have the similar feature. Compared with the other dFGAGs, dIBG has the strongest platelet activation activity, while dLGG having a lower negative charge loading capacity still has certain platelet activation activity. The results show that the platelet activation activities of FGAG and dFGAG are also associated with the sulfation patterns of the fucose branches.

The experimental results of this example show that the FGAG compositions with Fuc3S4S as main fucose branch have more advantageous anticoagulant antithrombotic activity, and have potent f.Xase inhibition activity and potent anticoagulant activity of HCII-dependent anti-f.IIa activity, but have no or less f.XII and platelet activation activity.

Example 7

Comparison of Anticoagulant Activities of dHSG Products Obtained by Different Depolymerization Methods 7.1 Materials (1) Fuc3S4S Substituted Oligoglycosaminoglycan Mixture Samples:

HSG-2 (Mw 63.5 kD, PDI1.06), the sample obtained in Example 2;

dHSG-4 (Mw 10.9 kD, PDI1.35), prepared by peroxide depolymerization;

dHSG-5 (Mw 7.5 kD, PDI1.28), prepared by deaminated depolymerization (terminal reduction);

dHSG-6 (Mw 8.4 kD, PDI1.33), β-eliminative depolymerization (terminal tyramine reductive amination)

(2) Reagents and Instruments:

The same as in Example 6.

7.2 Methods:

The same as in Example 6.

7.3 Results:

The anticoagulant activities of dHSG-4~-6 are shown in Table 8.

TABLE 8

Anticoagulant activities of HSG and its depolymerization products

| Sample | Anticoagulant activity | | | Effect on clotting factor activity | |
|---|---|---|---|---|---|
| | 2 × APTT[a] (μg/mL) | PT[b] (s) | TT[b] (s) | f.Xase[a] (ng/ml) | f.IIa/HCII[a] (ng/ml) |
| HSG-2 | 2.97 | 15.6 | 24.7 | 21.5 | 334 |
| dHSG-4 | 4.73 | 14.2 | 14.1 | 12.6 | 137 |
| dHSG-5 | 4.95 | 13.7 | 14.0 | 15.3 | 113 |
| dHSG-6 | 4.97 | 14.5 | 14.2 | 13.5 | 107 |

[a]the same as noted in Table 6;
[b]Coagulation time at a drug concentration of 16 μg/mL (PT, TT values in control group are 14.0 s and 13.6 s);

The results show that the HSG depolymerization products obtained by different methods have potent anticoagulant, f.Xase inhibition and HCII-dependent antithrombin activity. Wherein the anticoagulant activity is mainly expressed as the inhibition of endogenous coagulation (significant extension of APTT), and there is no effect on exogenous coagulation (no extension of PT). Prototype HSG-2 has a larger effect on common coagulation pathway (extension of TT, HSG-2 has an ATIII-dependent antithrombin activity), and the depolymerization samples have weaker effect on TT.

Example 8

Anticoagulant Activities of dHSGs with Different Molecular Weights 8.1 Materials (1) Samples:

Similar to the method for the preparation of HSG-2 in Example 1. HSG-a with Mw 63.6 kD was extracted and purified from commercially available dried *Holothuria scabra*, and further purified by ion exchange column chromatography and converted into Na$^+$ salt.

dHSG-1a (Mw 49.0 kD), dHSG-2a (Mw 27.8 kD), dHSG-3a (Mw 14.9 kD), dHSG-4a (Mw 8.24 kD), dHSG-5a (Mw 5.30 kD), dHSG-6a (Mw 3.12 kD) were all depolymerization products of HSG-a, prepared according to the depolymerization method similar to β-eliminative depolymerization in Example 1, and the reductive terminals were all reduced into alditol groups.

(2) Reagents and Instruments:

The same as in example 6.

8.2 Methods:

Same as in Example 6.

8.3 Results:

Anticoagulant activities of dHSG-1a~-6a are shown in Table 9 and FIG. 8.

TABLE 9

Anticoagulant activities of HSG and its depolymerization products

| Sample | Mw | 2 × APTT[a] (μg/mL) | f.Xase[a] (ng/mL) | HCII/IIa[a] (ng/mL) |
|---|---|---|---|---|
| HSG-a | 63.6 | 2.62 | 25.9 | 589.2 |
| dHSG-1a | 49.0 | 2.32 | 17.9 | 542.9 |
| dHSG-2a | 27.8 | 2.18 | 16.2 | 455.9 |
| dHSG-3a | 14.9 | 3.16 | 15.8 | 315.9 |
| dHSG-4a | 8.24 | 3.09 | 15.6 | 220.7 |
| dHSG-5a | 5.30 | 4.36 | 23.4 | 151.5 |
| dHSG-6a | 3.12 | 9.90 | 79.5 | 285.5 |
| LWMH | — | 6.55 | 81.8 | 230.8 |

[a]the same as noted in Table 6;

It can be seen from table 9 that, calculated based on mass concentration both the f.Xase inhibition activity and the HCII-dependent antithrombin activity of the depolymerization products with Mw in the range from 3 kD to 60 kD show a phenomenon of gradual increase and then decrease with the decrease of the molecular weight. The f.Xase inhibition activity is the strongest when Mw is about 8 kD, and the HCII-dependent antithrombin activity is the strongest when Mw is about 5 kD.

Previously it has been found from the research about the relationship between the anticoagulant activity of TAG depolymerization product and molecular weight that, Mw is less than about 10~12 kD, the f.Xase inhibition activity of TAG depolymerization products is gradually weakened, whereas when Mw is about 8 kD, the HCII-dependent antithrombin activity is basically similar and thereafter gradually weakened. Obviously, it can be seen from the correlation between molecular weight and anticoagulant activity that, the depolymerization product of HSG with lower molecular weight has more significant advantageous characteristics.

Considering the physicochemical property, pharmacological activity and safety of the polysaccharide compounds, the suitable weight-average molecular weights of HSG as well as the structure similar FGAG depolymerization product with Fuc3S4S as main focus component in the branch are in the range of about 3 kD-10 kD, and a more suitable weight-average molecular weight may be selected in the range of about 4.5 kD-9 kD.

Example 9

Preparation of Freeze-Dried Powder for Injection of Low-Molecular-Weight Fucosylated Glycosaminoglycan 9.1 Materials
dHSG:
prepared according to the method similar to dHSG-3a described in Examples 4, with 5. Mw ~5.5 kDa and PDI ~1.20.
9.2 Formula

| Name of raw material and excipient | Dosage |
| --- | --- |
| dHSG | 50 g |
| Water for injection | 500 mL |
| Prepared into | 1000 |

9.3 Preparation Process

The formulated low-molecular-weight fucosylated glycosaminoglycan sodium salt was weighed and added with water for injection to full capacity, stirred to dissolve completely, and subjected to interval autoclaving sterilization. 0.6% pharmaceutical activated carbon was added and stirred for 20 min. A Buchner funnel and a 3.0 m micro porous filter membrane were used for decarbonization filtration to remove pyrogens. The content of the intermediate was tested. The qualified products were passed through a 0.22 μm micro-porous filter membrane, filled into penicillin bottles with 0.5 mL in each bottle, partially stoppered, and transported into a lyophilizer and lyophilized according to the predetermined freeze-drying curve, completely stoppered, withdrawn from the lyophilizer, capped, inspected for qualification, and packed to obtain the final products.

Lyophilization procedure: Put the samples into the lyophilizer, lowered the temperature of shelves to −40° C. and kept at −40 for 3 hr. Lowered the temperature of cold trap was to −50° C., and the vacuum was pumped to 300 μbar. Sublimation: the temperature was increased at constant speed to −30° C. within 1 hr and maintained at −30° C. for 2 hr, Then the temperature was increased at constant speed to −20° C. within 2 hr and maintained at −20° C. for 8 hr, and the vacuum was maintained at 200-300 μbar. Drying: The temperature was increased to −5° C. within 2 hr and maintained at −5° C. for 2 hr, and the vacuum was maintained at 150-200 μbar. Then the temperature was increased to 10° C. within 0.5 hr, and maintained at 10° C. for 2 hr, and the vacuum was maintained at 80-100 bar. Then the temperature was increased to 40° C. within 0.5 hr and maintained at 40° C. for 4 hr, and the vacuum was reduced to the lowest.

What is claimed:

1. A Fuc3S4S substituted oligoglycosaminoglycan mixture or a pharmaceutically acceptable salt thereof, the Fuc3S4S is 3,4-disulfated-L-fucose-1-yl, the Fuc3S4S substituted oligoglycosaminoglycan mixture is a mixture of oligomeric homologous glycosaminoglycan compounds having a structure represented by Formula (I),

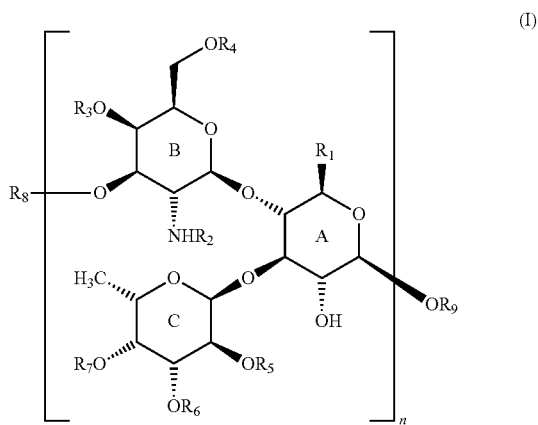

in Formula (I):
Ring A is β-D-glucuronic acid group or β-D-glucosyl group, wherein, R1 is —COO⁻ or —COR$_{10}$, R$_{10}$ is independently substituted or unsubstituted linear or branched C1-C6 alkyl, C7-C12 aralkyl;
Ring B is substituted β-D-2-amino-2-deoxy-galactosyl, wherein, R$_2$ is —COCH$_3$ or —H; R$_3$ and R$_4$ are independently —H or —SO$_3$⁻;
Ring C is α-L-fucosyl, wherein, R$_5$, R$_6$ and R$_7$ are independently —H or —SO$_3$⁻, and based on molar ratio, the α-L-fucosyl wherein R$_5$ is —H, R$_6$ and R$_7$ are —SO$_3$⁻, i.e. 3,4-disulfated-L-fucose-1-yl, accounts for not less than 75% of the total α-L-fucosyl;
R8 is the structure represented by Formula (III):

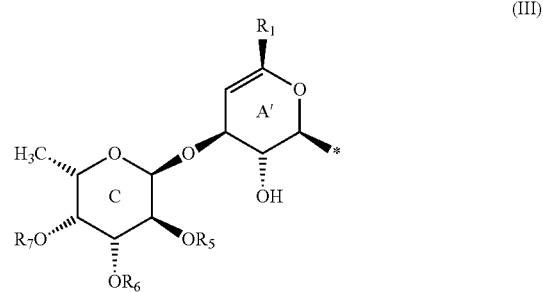

in Formula (III):
Ring A' is 4-deoxy-4-threo-hex-4-enopyranosyluronic acid group, R$_1$ in the formula is defined as above;
Ring C is α-L-fucosyl, wherein, R$_5$, R$_6$ and R$_7$ are defined as above;
R9 is a structure represented by Formula (IV) or Formula (V):

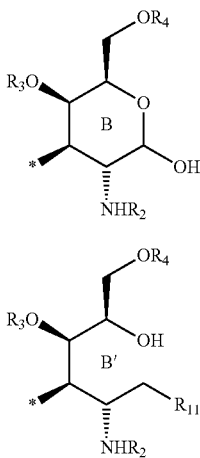

in Formula (IV) and (V),

Ring B is substituted α or β-D-2-amino-2-deoxy-galactosyl, B' is substituted 2-amino-2-deoxy-galactitol, glycosamine or N-substituted glucosamine, wherein, $R_3$ and $R_4$ are defined as above; $R_{11}$ is hydroxy, amino, C1-C6 alkylamino, C7-C12 arylamino;

n is an integer of 2-20; and based on molar ratio, the compound that n is 4-9 accounts for not less than 75% of the total compounds;

the oligomeric homologues glycosaminoglycan mixture has a weight average molecular weight (Mw) of 4.5-9 kD, and a polydispersity index (PDI) of less than or equal to 1.6, wherein the Fuc3S4S substituted oligoglycosaminoglycan mixture or a pharmaceutically acceptable salt thereof is produced by deacylated deaminated depolymerization or β-eliminative depolymerization.

2. The Fuc3S4S substituted oligoglycosaminoglycan mixture or pharmaceutically acceptable salt thereof of claim 1, wherein the mixture is a mixture of oligomeric homologues glycosaminoglycan compounds having a structure represented by Formula (VII), n is an integer of 3-15, based on molar ratio, the compounds which n is 4-9 account for not less than 75% of the total compounds;

based on molar ratio, in the compounds of Formula (VII), L-fucose-3,4-disulfated, i.e. α-L-Fuc3S4S group, accounts for not less than 75% of the total α-L-fucosyl;

and the oligomeric homologues glycosaminoglycan mixture has a weight-average molecular weight (Mw) of 4.5-9 kD.

3. The Fuc3S4S substituted oligoglycosaminoglycan mixture or a pharmaceutically acceptable salt thereof according to claim 1, wherein the oligoglycosaminoglycan mixture is prepared by chemical depolymerization of Fuc3S4S substituted glycosaminoglycan from sea cucumber, wherein the Fuc3S4S substituted glycosaminoglycan has the following features: monosaccharide composition comprises D-glucuronic acid, D-acetylgalactosamine and L-fucose in a molar ratio of 1:(1±0.3):(1±0.3); based on molar ratio, in the contained α-L-fucosyl, the proportion of 3,4-disulfated-α-L-fucosyl is no less than 75%.

4. The Fuc3S4S substituted oligoglycosaminoglycan mixture or a pharmaceutically acceptable salt thereof of claim 3, wherein the Fuc3S4S substituted glycosaminoglycan from sea cucumber is obtained by extracting and purifying fresh or dried body wall and/or viscus of *Holothuria scabra* or *Pearsonothuria graeffei*.

5. The Fuc3S4S substituted oligoglycosaminoglycan mixture or a pharmaceutically acceptable salt thereof of claim 1, wherein the pharmaceutically acceptable salt is sodium, potassium or calcium salt of the Fuc3S4S substituted oligoglycosaminoglycan mixture.

6. The Fuc3S4S substituted oligoglycosaminoglycan mixture or pharmaceutically acceptable salt thereof of claim 1, wherein the Fuc3S4S substituted oligoglycosaminoglycan mixture or a pharmaceutically acceptable salt thereof is produced without a step of carboxyl reduction with a carbodiimide compound.

7. The Fuc3S4S substituted oligoglycosaminoglycan mixture or a pharmaceutically acceptable salt thereof of claim 1, wherein the Fuc3S4S substituted oligoglycosaminoglycan mixture or a pharmaceutically acceptable salt thereof is

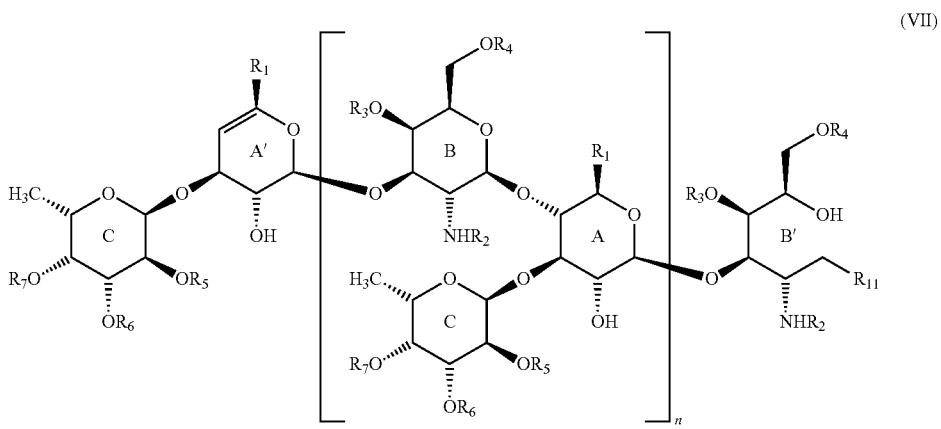

in Formula (VII):

chemical structure fragments A, A', B, B', C are defined as in claim 1;

$R_1$, $R_2$, $R_3$, $R_4$, $R_5$, $R_6$, $R_7$, $R_{11}$ are defined as in claim 1;

produced without a step of carboxyl reduction with a carbodiimide compound and a reducing agent.

8. The Fuc3S4S substituted oligoglycosaminoglycan mixture or pharmaceutically acceptable salt thereof of claim 1, wherein the at least one Ring A is a β-D-glucuronic acid group, wherein, $R_1$ is —COO—.

9. The Fuc3S4S substituted oligoglycosaminoglycan mixture or pharmaceutically acceptable salt thereof of claim 1, wherein Ring A is devoid of a D-glucosyl.

10. A pharmaceutical composition comprising the Fuc3S4S substituted oligoglycosaminoglycan mixture or a pharmaceutically acceptable salt thereof of claim 1, wherein the pharmaceutical composition comprises an anti-clotting effective amount of the oligoglycosaminoglycan mixture or a pharmaceutically acceptable salt thereof, and a pharmaceutical excipient and/or a pharmaceutical adjuvant.

11. The pharmaceutical composition of claim 10, wherein the pharmaceutical composition is in a dosage form of an aqueous solution for injection or freeze-dried powder for injection.

12. The pharmaceutical composition of claim 11, wherein the adjuvant of the pharmaceutical composition is a pharmaceutically acceptable sodium chloride, phosphate buffer.

13. The pharmaceutical composition of claim 10, wherein the Fuc3S4S substituted oligoglycosaminoglycan mixture or a pharmaceutically acceptable salt thereof is produced without a step of carboxyl reduction with a carbodiimide compound.

14. The pharmaceutical composition of claim 10, wherein the Fuc3S4S substituted oligoglycosaminoglycan mixture or a pharmaceutically acceptable salt thereof is produced without a step of carboxyl reduction with a carbodiimide compound and a reducing agent.

15. The pharmaceutical composition of claim 10, wherein the at least one Ring A is a β-D-glucuronic acid group, wherein, $R_1$ is —COO'.

16. The pharmaceutical composition of claim 10, wherein Ring A is devoid of a D-glucosyl.

17. A method of preparing the Fuc3S4S substituted oligoglycosaminoglycan mixture or pharmaceutically acceptable salt thereof of claim 1, the method comprising:

obtaining a polysaccharide composition containing a Fuc3S4S substituted glycosaminoglycan;

performing quaternary ammonium transalification;

performing carboxyl esterification;

performing β-eliminative depolymerization; and performing purification to obtain the Fuc3S4S substituted oligoglycosaminoglycan mixture or a pharmaceutically acceptable salt thereof, wherein the Fuc3S4S is 3,4-disulfated-L-fucose-1-yl, wherein the Fuc3S4S substituted oligoglycosaminoglycan mixture is a mixture of the oligomeric homologous glycosaminoglycan compounds, the method being performed without a step of carboxyl reduction with a carbodiimide compound.

18. A method for treating thrombotic diseases, comprising administering to a patient in need of a therapeutically or prophylactically effective amount of the pharmaceutical composition of claim 10 to provide the anti-clotting effect.

* * * * *